(12) United States Patent
Dummer et al.

(10) Patent No.: US 9,394,550 B2
(45) Date of Patent: Jul. 19, 2016

(54) LAURIC ESTER COMPOSITIONS

(71) Applicant: TerraVia Holdings, Inc., South San Francisco, CA (US)

(72) Inventors: Timothy Dummer, South San Francisco, CA (US); Risha Bond, South San Francisco, CA (US)

(73) Assignee: TerraVia Holdings, Inc., South San Francisco, CA (US)

( * ) Notice: Subject to any disclaimer, the term of this patent is extended or adjusted under 35 U.S.C. 154(b) by 0 days.

(21) Appl. No.: 14/671,894

(22) Filed: Mar. 27, 2015

(65) Prior Publication Data

US 2015/0275149 A1    Oct. 1, 2015

Related U.S. Application Data

(60) Provisional application No. 61/972,026, filed on Mar. 28, 2014.

(51) Int. Cl.
| | | |
|---|---|---|
| *C12P 7/64* | (2006.01) | |
| *C11D 7/26* | (2006.01) | |
| *C07C 67/03* | (2006.01) | |
| *C11C 3/08* | (2006.01) | |
| *C11D 3/20* | (2006.01) | |
| *C11D 7/24* | (2006.01) | |
| *C11C 3/00* | (2006.01) | |

(52) U.S. Cl.
CPC .............. *C12P 7/6436* (2013.01); *C07C 67/03* (2013.01); *C11C 3/08* (2013.01); *C11D 3/2093* (2013.01); *C11D 7/266* (2013.01); *C11C 3/00* (2013.01); *C11D 7/248* (2013.01)

(58) Field of Classification Search
None
See application file for complete search history.

(56) References Cited

U.S. PATENT DOCUMENTS

| | | | |
|---|---|---|---|
| 2,383,602 | A | 8/1945 | Gerald et al. |
| 3,280,502 | A | 10/1966 | Farrow et al. |
| 3,962,466 | A | 6/1976 | Nakabayashi |
| 4,103,039 | A | 7/1978 | Mandai et al. |
| 4,140,805 | A | 2/1979 | Edwards et al. |
| 4,341,038 | A | 7/1982 | Bloch et al. |
| 4,390,561 | A | 6/1983 | Blair et al. |
| 4,627,192 | A | 12/1986 | Fick |
| 4,673,490 | A | 6/1987 | Subramanian et al. |
| 5,001,059 | A | 3/1991 | Skatrud et al. |
| 5,130,242 | A | 7/1992 | Barclay et al. |
| 5,252,198 | A | 10/1993 | Harrison et al. |
| 5,338,673 | A | 8/1994 | Thepenier et al. |
| 5,354,878 | A | 10/1994 | Connemann et al. |
| 5,492,938 | A | 2/1996 | Kyle et al. |
| 5,518,918 | A | 5/1996 | Barclay |
| 5,547,699 | A | 8/1996 | Lizuka et al. |
| 5,595,965 | A | 1/1997 | Wiggins |
| 5,711,983 | A | 1/1998 | Kyle et al. |
| 5,888,947 | A | 3/1999 | Lambert et al. |
| 5,945,585 | A | 8/1999 | Hitz et al. |
| 5,968,791 | A | 10/1999 | Davis et al. |
| 6,139,897 | A | 10/2000 | Goto et al. |
| 6,255,505 | B1 | 7/2001 | Bijl et al. |
| 6,338,866 | B1 | 1/2002 | Criggall et al. |
| 6,441,208 | B2 | 8/2002 | Bijl et al. |
| 6,620,427 | B2 | 9/2003 | Lasekan et al. |
| 6,727,373 | B2 | 4/2004 | Bijl et al. |
| 7,053,267 | B2 | 5/2006 | Knauf et al. |
| 7,063,957 | B2 | 6/2006 | Chen |
| 7,504,259 | B2 | 3/2009 | Yadav et al. |
| 7,588,931 | B2 | 9/2009 | Damude et al. |
| 7,652,156 | B2 | 1/2010 | Hillion et al. |
| 7,879,591 | B2 | 2/2011 | Damude et al. |
| 7,883,882 | B2 | 2/2011 | Franklin et al. |
| 7,935,515 | B2 | 5/2011 | Franklin et al. |
| 8,029,579 | B2 | 10/2011 | Knuth et al. |
| 8,088,718 | B2 | 1/2012 | Bicerano et al. |
| 8,119,583 | B2 | 2/2012 | Day et al. |
| 8,187,860 | B2 | 5/2012 | Franklin et al. |
| 8,222,010 | B2 | 7/2012 | Franklin et al. |
| 8,268,610 | B2 | 9/2012 | Franklin et al. |
| 8,278,261 | B2 | 10/2012 | Day et al. |
| 8,283,483 | B2 | 10/2012 | Williams et al. |
| 8,435,767 | B2 | 5/2013 | Franklin et al. |
| 8,450,083 | B2 | 5/2013 | Day et al. |
| 8,476,059 | B2 | 7/2013 | Trimbur et al. |
| 8,497,116 | B2 | 7/2013 | Trimbur et al. |

(Continued)

FOREIGN PATENT DOCUMENTS

| | | |
|---|---|---|
| CN | 1940021 A | 4/2007 |
| CN | 101037639 A | 9/2007 |

(Continued)

OTHER PUBLICATIONS

Elumalai, S., et al., Optimizatin of abiotic conditions suitable for the production of biodiesel from Chlorella vulgaris, 2011, Indian Journal of Science and Technology, vol. 4, No. 2, pp. 91-97.*
Phippen, W. B., et al., Total seed oil and fatty acid methyl ester contents of Cuphea accessions, 2006, Industrial crops and products, vol. 24, No. 1, pp. 52-59.*
"Soybean Oil Innovations, 3rd Edition," United Soybean Board, www.soyconnection.com, 8 pages, (2009). [Available from the Internet on Jan. 15, 2009: <URL: http://www.soyconnection.com/sites/default/files/soy-oil-solutions.pdf>].
"Codex Standard for Named Vegetable Oils," CODEX Alimentarius, CODEX STAN 210-1999, pp. 1-16, (1999).
Aggelis et al., "Enhancement of single cell oil production by Yarrowia lipolytica growing in the presence of *Teucrium polium* L. aqueous extract," Biotechnology Letters, 21:747-749, (1999).

(Continued)

*Primary Examiner* — Yate K Cutliff
(74) *Attorney, Agent, or Firm* — Weaver Austin Villeneuve & Sampson, LLC.

(57) ABSTRACT

Provided are compositions containing alkyl esters derived from triglyceride oils produced from genetically engineered microalgae. Specific embodiments relate to esters derived from oils with high C10-C12 fatty acid profile. Compositions comprising the esters include cleaning products, completion fluids, work-over fluids, drilling fluids, metal working fluids, lubricants, paints, and inks.

16 Claims, No Drawings

(56) References Cited

U.S. PATENT DOCUMENTS

| | | | |
|---|---|---|---|
| 8,512,999 B2 | 8/2013 | Trimbur et al. |
| 8,518,689 B2 | 8/2013 | Trimbur et al. |
| 8,530,207 B2 | 9/2013 | Watts et al. |
| 8,592,188 B2 | 11/2013 | Franklin et al. |
| 8,617,317 B1 | 12/2013 | Levitt |
| 8,633,012 B2 | 1/2014 | Franklin et al. |
| 8,647,397 B2 | 2/2014 | Trimbur et al. |
| 8,674,180 B2 | 3/2014 | Franklin et al. |
| 8,697,402 B2 | 4/2014 | Trimbur et al. |
| 8,697,427 B2 | 4/2014 | Franklin et al. |
| 8,765,424 B2 | 7/2014 | Franklin et al. |
| 8,772,575 B2 | 7/2014 | Franklin et al. |
| 8,790,914 B2 | 7/2014 | Trimbur et al. |
| 8,802,422 B2 | 8/2014 | Trimbur et al. |
| 8,822,176 B2 | 9/2014 | Day et al. |
| 8,822,177 B2 | 9/2014 | Day et al. |
| 8,846,352 B2 | 9/2014 | Chua et al. |
| 8,846,375 B2 | 9/2014 | Franklin et al. |
| 8,852,885 B2 | 10/2014 | Franklin et al. |
| 8,889,401 B2 | 11/2014 | Trimbur et al. |
| 8,889,402 B2 | 11/2014 | Trimbur et al. |
| 8,945,908 B2 | 2/2015 | Franklin et al. |
| 8,951,777 B2 | 2/2015 | Franklin et al. |
| 9,062,294 B2 | 6/2015 | Franklin et al. |
| 9,066,527 B2 | 6/2015 | Franklin et al. |
| 9,068,213 B2 | 6/2015 | Franklin et al. |
| 2002/0122868 A1 | 9/2002 | Floeter et al. |
| 2003/0097686 A1 | 5/2003 | Knauf et al. |
| 2003/0229237 A1 | 12/2003 | Haas et al. |
| 2004/0033557 A1 | 2/2004 | Scott et al. |
| 2004/0230085 A1 | 11/2004 | Jakkula et al. |
| 2005/0005333 A1 | 1/2005 | Ruezinsky et al. |
| 2005/0262588 A1 | 11/2005 | Dehesh et al. |
| 2005/0266537 A1 | 12/2005 | Chen |
| 2005/0272611 A1 | 12/2005 | Lord et al. |
| 2006/0094088 A1 | 5/2006 | Picataggio et al. |
| 2006/0094089 A1 | 5/2006 | Barclay |
| 2007/0099280 A1 | 5/2007 | Barclay |
| 2007/0167396 A1 | 7/2007 | Dillon et al. |
| 2007/0218183 A1 | 9/2007 | Nakhasi et al. |
| 2007/0248531 A1 | 10/2007 | Debryun et al. |
| 2007/0261138 A1 | 11/2007 | Graham et al. |
| 2008/0160593 A1 | 7/2008 | Oyler |
| 2008/0206379 A1 | 8/2008 | Fabritius et al. |
| 2008/0283803 A1 | 11/2008 | Rapp et al. |
| 2009/0004715 A1 | 1/2009 | Trimbur et al. |
| 2009/0061493 A1 | 3/2009 | Trimbur et al. |
| 2009/0064567 A1 | 3/2009 | Lippmeier et al. |
| 2009/0099260 A1 | 4/2009 | Namal Senanayake et al. |
| 2009/0234146 A1 | 9/2009 | Cooney et al. |
| 2009/0274736 A1 | 11/2009 | Dillon et al. |
| 2010/0021912 A1 | 1/2010 | Farese et al. |
| 2010/0035309 A1 | 2/2010 | Havemen et al. |
| 2010/0058651 A1 | 3/2010 | Knuth et al. |
| 2010/0120643 A1 | 5/2010 | Brown et al. |
| 2010/0151112 A1 | 6/2010 | Franklin et al. |
| 2010/0151538 A1 | 6/2010 | Franklin et al. |
| 2010/0170144 A1 | 7/2010 | Day et al. |
| 2010/0186117 A1 | 7/2010 | Fabijanski et al. |
| 2010/0196575 A1 | 8/2010 | Sanchez et al. |
| 2010/0228068 A1 | 9/2010 | O'Connor et al. |
| 2010/0239712 A1 | 9/2010 | Brooks et al. |
| 2010/0248321 A1 | 9/2010 | Steaffens et al. |
| 2010/0248322 A1 | 9/2010 | Pfeiffer et al. |
| 2010/0297292 A1 | 11/2010 | Brooks et al. |
| 2010/0297295 A1 | 11/2010 | Brooks et al. |
| 2010/0297296 A1 | 11/2010 | Brooks et al. |
| 2010/0297323 A1 | 11/2010 | Brooks et al. |
| 2010/0297325 A1 | 11/2010 | Brooks et al. |
| 2010/0297331 A1 | 11/2010 | Brooks et al. |
| 2010/0303957 A1 | 12/2010 | Brooks et al. |
| 2010/0303961 A1 | 12/2010 | Brooks et al. |
| 2010/0303989 A1 | 12/2010 | Brooks et al. |
| 2010/0303990 A1 | 12/2010 | Brooks et al. |
| 2010/0323414 A1 | 12/2010 | Trimbur et al. |
| 2011/0047863 A1 | 3/2011 | Trimbur et al. |
| 2011/0065821 A1 | 3/2011 | Abraham et al. |
| 2011/0190522 A1 | 8/2011 | Trimbur et al. |
| 2011/0203168 A1 | 8/2011 | Franklin et al. |
| 2011/0252696 A1 | 10/2011 | Franklin et al. |
| 2011/0256268 A1 | 10/2011 | Franklin et al. |
| 2011/0256282 A1 | 10/2011 | Piechocki et al. |
| 2011/0284215 A1 | 11/2011 | Pfeiffer et al. |
| 2011/0293785 A1 | 12/2011 | Franklin et al. |
| 2012/0021495 A1 | 1/2012 | Vanzin |
| 2012/0034662 A1 | 2/2012 | Hu et al. |
| 2012/0128851 A1 | 5/2012 | Brooks et al. |
| 2012/0156717 A1 | 6/2012 | Allnutt et al. |
| 2012/0164701 A1 | 6/2012 | Trimbur et al. |
| 2012/0203018 A1 | 8/2012 | Franklin et al. |
| 2013/0004646 A1 | 1/2013 | Franklin et al. |
| 2013/0006006 A1 | 1/2013 | Day et al. |
| 2013/0031678 A1 | 1/2013 | Zheng et al. |
| 2013/0096211 A1 | 4/2013 | Franklin et al. |
| 2013/0102039 A1 | 4/2013 | Franklin et al. |
| 2013/0122180 A1 | 5/2013 | Brooks et al. |
| 2013/0157917 A1* | 6/2013 | Fluck .................. C11D 3/2093 510/109 |
| 2013/0165677 A1 | 6/2013 | Franklin et al. |
| 2013/0197247 A1 | 8/2013 | Franklin et al. |
| 2013/0316410 A1* | 11/2013 | Franklin .............. C12P 7/6463 435/134 |
| 2013/0317240 A1 | 11/2013 | Franklin et al. |
| 2013/0323382 A1 | 12/2013 | Franklin et al. |
| 2013/0330790 A1 | 12/2013 | Trimbur et al. |
| 2013/0338385 A1 | 12/2013 | Franklin et al. |
| 2014/0170716 A1 | 6/2014 | Trimbur et al. |
| 2014/0256024 A1 | 9/2014 | Franklin et al. |
| 2014/0256600 A1 | 9/2014 | Dillon et al. |
| 2014/0305031 A1 | 10/2014 | Day et al. |
| 2014/0315267 A1 | 10/2014 | Franklin et al. |
| 2014/0336100 A1 | 11/2014 | Day et al. |
| 2014/0357746 A1 | 12/2014 | Ngantung et al. |
| 2014/0377847 A1 | 12/2014 | Franklin et al. |
| 2015/0031929 A1* | 1/2015 | Asoaka .................. C10L 1/04 585/733 |
| 2015/0073163 A1 | 3/2015 | Chua et al. |
| 2015/0125914 A1 | 5/2015 | Franklin et al. |
| 2015/0218604 A1 | 8/2015 | Franklin et al. |
| 2015/0305362 A1 | 10/2015 | Rakitsky et al. |
| 2015/0344917 A1 | 12/2015 | Franklin et al. |
| 2015/0374012 A1 | 12/2015 | Klamczynska et al. |
| 2016/0021923 A1 | 1/2016 | Paulsen et al. |
| 2016/0024538 A1 | 1/2016 | Franklin et al. |

FOREIGN PATENT DOCUMENTS

| | | |
|---|---|---|
| CN | 101130513 | 2/2008 |
| EP | 0562504 B1 | 11/1995 |
| EP | 1681337 A1 | 7/2006 |
| EP | 1741767 A1 | 1/2007 |
| EP | 2152849 B1 | 2/2013 |
| GB | 824151 A | 11/1959 |
| IN | 2296/MUM/2012 | 9/2012 |
| JP | 06-253872 A | 9/1994 |
| JP | 07-008217 | 1/1995 |
| JP | 07-075557 | 3/1995 |
| JP | 2002-125601 | 5/2002 |
| JP | 2008-148663 | 7/2008 |
| WO | WO 94/10288 A2 | 5/1994 |
| WO | WO 97/40698 A1 | 11/1997 |
| WO | WO 99/37166 A1 | 7/1999 |
| WO | WO 00/11682 A1 | 3/2000 |
| WO | WO 00/61740 A1 | 10/2000 |
| WO | WO 00/66750 A2 | 11/2000 |
| WO | WO 00/74471 A1 | 12/2000 |
| WO | WO 02/08403 A2 | 1/2002 |
| WO | WO 2007/027669 A1 | 3/2007 |
| WO | WO 2007/117511 A2 | 10/2007 |
| WO | WO 2007/121100 A2 | 10/2007 |
| WO | WO 2007/134294 A2 | 11/2007 |
| WO | WO 2008/002643 A2 | 1/2008 |
| WO | WO 2008/060571 A2 | 5/2008 |
| WO | WO 2008/083352 A1 | 7/2008 |

(56) References Cited

FOREIGN PATENT DOCUMENTS

| WO | WO 2008/130372 A2 | 10/2008 |
|---|---|---|
| WO | WO 2008/134836 A2 | 11/2008 |
| WO | WO 2008/151149 A2 | 12/2008 |
| WO | WO 2009/076559 A1 | 6/2009 |
| WO | WO 2009/105620 A1 | 8/2009 |
| WO | WO 2009/126843 A2 | 10/2009 |
| WO | WO 2010/019813 A2 | 2/2010 |
| WO | WO 2010/045368 A2 | 4/2010 |
| WO | WO 2010/063031 A2 | 6/2010 |
| WO | WO 2010/063032 A2 | 6/2010 |
| WO | WO 2010/111698 A2 | 9/2010 |
| WO | WO 2010/120923 A1 | 10/2010 |
| WO | WO 2010/120939 A2 | 10/2010 |
| WO | WO 2011/026008 A1 | 3/2011 |
| WO | WO 2011/090730 A1 | 7/2011 |
| WO | WO 2011/130573 A1 | 10/2011 |
| WO | WO 2011/130576 A1 | 10/2011 |
| WO | WO 2011/130578 A2 | 10/2011 |
| WO | WO 2011/150410 A2 | 12/2011 |
| WO | WO 2011/150411 A1 | 12/2011 |
| WO | WO 2012/061647 A2 | 5/2012 |
| WO | WO 2012/106560 A1 | 8/2012 |
| WO | WO 2012/154626 A1 | 11/2012 |
| WO | WO 2013/082186 A2 | 6/2013 |
| WO | WO 2013/096891 | 6/2013 |
| WO | WO 2013/158938 | 10/2013 |
| WO | WO 2014/176515 A2 | 10/2014 |
| WO | WO 2015/051319 A2 | 4/2015 |

OTHER PUBLICATIONS

Aguirre et al., "Engineering challenges in biodiesel production from microalgae," Critical Reviews in Biotechnology, 33(3): 293-308, (2013).
Amaro et al., "Advances and perspectives in using microalgae to produce biodiesel," Applied Energy, 88:3402-3410, (2011).
Andersen, "Biology and Systematics of Heterokont and Haptophyte Algae," American Journal of Botany, 91(10):1508-1522, (2004).
Barnes et al., "Contribution of 5'- and 3'-untranslated regions of plastid mRNAs to the expression of Chlamydomonas reinhardtii chloroplast genes," Mol Genet Genomics, 274(6):625-636, (2005).
Beale et al., "Chlorophyll Synthesis in Chlorella: Regulation by Degree of Light Limitation of Growth," Plant Physiol., 47:230-235, (1971).
Bhunia et al., "Algal Biodiesel Production: Challenges and Opportunities," Bioenergy and Biofuel from Biowastes and Biomass, American Society of Civil Engineers, pp. 313-345, (2010).
Bigogno et al., "Biosynthesis of arachidonic acid in the oleaginous microalga Parietochloris incisa (Cholorphyceae): Radiolabeling studies," Lipids 37(2):209-216 (2002); Abstract Only.
Bigogno et al., "Lipid and fatty acid composition of the green oleaginous alga Parietochloris incise, the richest plant source of arachidonic acid," Pytochemistry, 60:497-503, (2002).
Blowers et al., "Studies on Chlamydomonas chloroplast transformation: foreign DNA can be stably maintained in the chromosome," Plant Cell, 1(1):123-132, (1989).
Bonaventure et al., "Disruption of the FATB Gene in Arabidopsis Dethonstrates an Essential Role of Saturated Fatty Acids in Plant Growth," The Plant Cell 15:1020-1033, (2003).
Bornscheuer et al. (ed), "Enzymes in Lipid Modification," Wiley-VCH Verlag Gmbh & Co. KGaA, 1st Edition, ISBN: 3-527-30176-3, Sections 1-11, 231 pages, (2000). (part 1 of 2 of book).
Bornscheuer et al. (ed), "Enzymes in Lipid Modification," Wiley-VCH Verlag Gmbh & Co. KGaA, 1st Edition, ISBN: 3-527-30176-3, Sections 12-18, 133 pages, (2000). (part 2 of 2 of book).
Borza et al., "Multiple Metabolic Roles for the Nonphotosynthetic Plastid of the Green Alga Prototheca Wickerhamii," Eukaryotic Cell, 4(2):253-261, (2005).
Broun et al., "Accumulation of Ricinoleic, Lesquerolic, and Densipolic Acids in Seeds of Transgenic Arabidopsis Plants That Express a Fatty Acyf Hydroxylase cDNA from Castor Bean," Plant Physiol., 113:933-942, (1997).

Brown et al., "The amino-acid and sugar composition of 16 species of micralgae used in mariculture," J. Exp. Mar. Biol. Ecol. 145:79-99 abstract (1991).
Burgal et al., "Metabolic engineering of hydroxy fatty acid production in plants: RcDGAT2 drives dramatic increases in ricinoleate levels in seed oil," Plant Biotechnol J., 6(8):819-831, (2008).
Cartens et al,. "Eicosapentaenoic Acid (20:5n-3) from the Marine Microalga Phaeodactylum tricornutum," Journal of the American Oil Chemists' Society, 73(8):1025-1031, (1996).
Chen et al., "Effect of C/N ratio and aeration on the fatty acid composition of heterotrophic Chlorella sorokiniana," Journal of Applied Phycology, 3:203-209, (1991).
Ciferri, "Thiamine-deficiency of Prototheca, a Yeast-like Achloric Alga," Nature, 178:1475-1476, (1956).
Co et al., "Matching the Functionality of Single-Cell Algal Oils with Different Molecular Compositions," J Am Oil Chem Soc, doi: 10.1007/s11746-013-2405-y, 16 pages, (2014).
Cohen et al., "The Heterotrophic Connection in a Photoautotrophic Chlorella Vulgaris Dominant in W Astew Ater Oxidation Ponds," War. Sci. Tech., 27(7-8):151-155, (1993).
Cordy et al., "Chlorellasis in a Lamb," Vet. Path., 10:171-176, (1973).
Courchesne et al., "Enhancement of Lipid Production Using Biochemical, Genetic and Transcription Factor Engineering Approaches," J Biotechnol. Epub, 141(1-2):31-41, (2009).
Davies et al.,"Expression of the Arylsulfatase Gene from the Beta 2-Tubulin Promoter in Chlamydomonas reinhardtii," Nucleic Acids Research, 20(12):2959-2965, (1992).
Day, AL. et al., "Safety evaluation of a high-lipid algal biomass from Chlorella protorhecoides," Regol. Toxicol. Pharmacol., doi:10.1016/j.yrtph.2009.06.014, 15 pages, (2009).
De Cock, "Structure development in confectionery products: importance of triacylglycerol composition," Master Thesis, Masters in Bioscience Engineering, Ghent University, 73 pages, (2011).
Debuchy et al., "The argininosuccinate lyase gene of Chlamydomonas reinhardtii: an important tool for nuclear transformation and for correlating the genetic and molecular maps of the ARG7 locus," EMBO J., 8(10):2803-2809, (1989).
Dehesh et al., "Kas IV: a 3-ketoacyl-ACP synthase from Cuphea sp. is a medium chain specific condensing enzyme," The Plant Journal, 15:383-390, (1998).
Dehesh et al., "Production of high levels of 8:0 and 10:0 fatty acids in transgenic canola by overexpression of Ch FatB2, a thioesterase cDNA from Cuphea hookeriana," The Plant Journal, 9(2):167-172, (1996).
Demirbas et al., "Importance of algae oil as a source of biodiesel," Energy Conversion and Management, 52:163-170, (2011).
Deng et al., "Ionic Liquid as a Green Reaction Medium for Esterifications," J. Mol. Catalysis A: Chemical, 165:33-36, (2001).
Deshnium et al., "Transformation of Synechococcus with a gene for choline oxidase enhances tolerance to salt stress," Plant Mol Biol, 29(5):897-907, (1995).
Dunahay et al., "Genetic Engineering of Microalgae for Fuel Production," Applied Biochemistry and Biotechnology, 34/35:331-339 (1992).
Dunahay et al., "Manipulation of Microalgal Lipid Production Using Genetic Engineering," Applied Biochemistry and Biotechnology, 57/58:223-231, (1996).
El-Fadaly et al., "Single Cell Oil Production by an Oleaginous Yeast Strain in a Low Cost Cultivation Medium," Research Journal of Microbiology, 4(8):301-313, (2009).
EPO Supplementary European Search Report and European Search Opinion for application EP 12782478.7 mailed Oct. 22, 2014.
EPO Supplementary European Search Report and European Search Opinion for application EP08769988.0 mailed Jul. 1, 2011.
EPO Supplementary European Search Report and European Search Opinion for application EP1158642.6 mailed Jul. 1, 2011.
EPO Supplementary European Search Report and European Search Opinion for application EP09829850.8 mailed May 16, 2014.
EPO Supplementary European Search Report and European Search Opinion for application EP09729658 mailed Jan. 3, 2013.
Erhan, "Vegetable Oils as Lubricants, Hydraulic Fluids, and Inks," Bailey's Industrial Oil and Fat Products, 6:259-278, (2005).

(56) References Cited

OTHER PUBLICATIONS

Evans et al., "A comparison of the oleaginous yeast, Candida curvata, grown on different carbon sources in continous and batch culture," Lipids, 18(09):623-629, (1983).
Fall et al., "Bioconversion of Xylan to Triglycerides by Oil-Rich Yeasts," Applied and Environmental Microbiology, 47(5):1130-1134, (1984).
Fernandez-Reiriz et al., "Biomass Production and Variation in the Biochemical Profile (Total Protein, Carbohydrates, RNA, Lipids and Fatty Acids) of Seven Species of Marine Microalgae," Aquaculture, 83:17-37, (1989).
Ferrentino, "Microalgal oil extraction and in situ transesterification," University of New Hampshire, Pub. No. MT 1447885, 8 pages, (2007).
Ferrentino, et al., "Microalgal Oil Extraction and In-situ Transesterification," AIChE Annual Mtg, San Francisco, CA, Nov. 11-13, 2006. Abstract.
Franzen et al., "Chloroplast transit peptides from the green alga Chlamydomonas reinhardtii share features with both mitochondrial and higher plant chloroplast presequences," FEBS Letters, 260(2):165-168, (1990).
Frenz et al., "Hydrocarbon recovery by extraction with a biocompatible solvent from free and immobilized cultures of Botryococcus braunii," Enzyme Microb Technol, 11(11):717-724, (1989).
Frohns et al., "Potassium ion channels of Chlorella viruses cause rapid depolarization of host cells during infection," J Virol, 80(5):2437-2444, (2006).
Fukuda et al., "Biodiesel Fuel Production by Transesterification of Oils," J. Biosci. Bioeng., 92(5):405-416, (2001).
Funes et al., "The typically mitochondrial DNA-encoded ATP6 subunit of the F1F0-ATPase is encoded by a nuclear gene in Chlamydomonas reinhardtii," J Biol Chem, 277(8):6051-6058, (2002).
Gill et al., "Lipid Accumulation in an Oleaginous Yeast (Candida 107) Growing on Glucose in Single-Stage Continuous Culture," Applied and Environmental Microbiology, 33(02):231-239, (1977).
Gonzalez et al., "Optimization of Fatty Add Extraction from Phaeodactylum tricornutum UTEX 640 Biomass," JAOCS, 75(12):1735-1740, (1998).
Gouveia et al., "Microalgae in Novel Food Products," Food Chemistry Research Developments, Chapter 2, Nova Science Publishers, Inc., ISBN 978-1-60456-262-0, 37 pages, (2008).
Graves et al., "Hyaluronan synthesis in virus PBCV-1-infected chlorella-like green algae," Virology, 257(1):15-23, (1999).
Grima et al., "Recovery of microalgal biomass and metabolites: process options and economics," Biotechnology Advances, 20:491-515, (2003).
Guiry et al., "How Many Species of Algae are There?," J. Phycol., 48:1057-1063, (2012).
Gul et al., "Sterols and the Phytosterol Content in Oilseed Rape (*Brassica napus* L.)," Journal of Cell and Molecular Biology, 5:71-79 (2006).
Gunstone, "Enzymes as biocatalysts in the modification of natural lipids," Journal of the Science of Food and Agriculture, 79:1535-1549, (1999).
Guschina et al., "Lipids and lipid metabolism in eukaryotic algae," Progress in Lipid Research, 45:160-186, (2006).
Haas et al., "The General Applicability of in Situ Transesterification for the Production of Fatty Acid Esters from a Variety of Feedstocks," J Am Oil Chem Sac, 84:963-970, (2007).
Hall et al., "Expression of a foreign gene in Chlamydomonas reinhardtii," Gene, 124(1):75-81, (1993).
Hall et al., "Lipid Accumulation in an Oleaginous Yeast (Candida 107) Growing on Glucose Under Various Conditions in a One- and Two-Stage Continuous Culture," Applied and Environmental Microbiology, 33(3):577-584, (1977).
Heise et al., "Factors Controlling Medium-Chain Fatty Acid Synthesis in Plastids From Cuphea Embryos," Prog. Lipid Res., 33(1/2):87-95, (1994).
Henderson et al., "Lipid Composition and Biosynthesis in the Marine Dinoflagellate Crypthecodznzum Cohnii," Phytochem. 27(6)1679-1683 (1988).
Heredia et al., "Simultaneous utilization of glucose and xylose by *Candida curvata* D in continuous culture," Biotechnology Letters, 10(01):25-30, (1988).
Heredia-Arroyo et al., "Oil Accumulation via Heterotrophic/Mixotrophic Chlorella protothecoides," Appl Biochem Biotechnol, 162:1978-1995, (2010).
Hillen et al., "Hydrocracking of the Oils of Botryococcus braunii to Transport Fuels," Biotechnology and Bioengineering, 24(1)193-205, (1982).
Hiramatsu et al., "Expression of a chitinase gene and lysis of the host cell wall during Chlorella virus CVK2 infection," Virology, 260(2):308-315, (1999).
Hitz et al.,"Cloning of a Higher-Plant Plastid Omega-6 Fatty Acid Desaturase cDNA and Its Expression in a Cyanobacterium," Plant Physiology, 105(2):635-641, (1994).
Hu et al., "Microalgal Triacylglycerols as Feedstocks for Biofuel Production: Perspectives and Advances," The Plant Journal 54:621-639, (2008).
Huang et al., "Expression of Mercuric Reductase From Bacillus Megaterium MB1 in Eukaryotic Microalga *Chlorella* sp. DT: An Approach for Mercury Phytoremediation," Appl. Microbiol. Biotechnol., 72:197-205, (2006).
Huber et al, "Production of Liquid Alkanes by Aqueous-Phase Processing of Biomass-Derived Carbohydrates," Science, 308:1446-1450, (2005).
Huber et al., "Synthesis of Transportation Fuels from Biomass: Chemistry, Catalysts, and Engineering," Chem. Rev., 106: 4044-4098, (2006).
Inoue et al., "Analysis of oil derived from liquefaction of Botryococcus Braunii," Biomass and Bioenergy, 6(4):269-274, (1994).
Jakobiak et al., "The Bacterial Paromomycin Resistance Gene, aphH, as a Dominant Selectable Marker in Volvox carteri," Protist, 55: 381-393, (2004).
Jaworski et al., "Industrial oils from transgenic plants," Current Opinion in Plant Biology, 6:178-184, (2003).
Jiang et al., "The actin gene promoter-driven bar as a dominant selectable marker for nuclear transformation of Dunaliella salina," Yi Chuan Xue Bao, 32(4):424-433, (2005).
Kamiya, "Effects of Blue Light and Ammonia on Nitrogen Metabolism in a Colorless Mutant of Chlorella," Plant Celll Physiol., 30(4):513-521, (1989).
Kang et al., "Genetic diversity in chlorella viruses flanking kcv, a gene that encodes a potassium ion channel protein," Virology, 326(1)150-159, (2004).
Kang et al., "The regulation activity of Chlorella virus gene 5' upstream sequence in *Escherichia coli* and eucaryotic alage," Institute of Microbiology, Chinese Academy of Sciences, Beijing, 16(4):443-6, (2000). Abstract only.
Karabulut et al., "Determination of changes in some physical and chemical properties of soybean oil during hydrogenation," Food Chemistry, 81:453-456, (2003).
Katayama et al., "Alpha-Linolenate and Photosynethetic Activity in Chlorella Protothecoides," Plant Physiol., 42:308-313, (1967).
Kawasaki et al., "Characterization of Immediate Early Genes Expressed in Chlorovirus Infections," Nucleic Acids Symp Ser, 44:161-162, (2000).
Kawasaki et al., "Immediate Early Genes Expressed in Chlorovirus Infections," Virology, 318(1):214-223, (2004).
Kenyon, "Fatty Acid Composition of Unicellular Strains of Blue-Green Algae," J. Bacteriology 109(2):827-834 (1972).
Kindle, "High-Frequency Nuclear Transformation of Chlamydomonas reinhardtii," Proc Natl Acad Sci, 87(3):1228-1232, (1990).
Knothe, "Designer' Biodiesel: Optimizing Fatty Ester Composition to Improve Fuel Properties," Energy & Fuels, 22:1358-1364, (2008).
Kong et al., "Microbial production of lipids by cofermentation of glucose and xylose with Lipomyces starkeyi 2#," Chinese Journal of Bioprocess Engineering, 05(02):36, (2007). Abstract.
Kris-Etherton et al., "Monounsaturated Fatty Acids and Risk of Cardiovascular Disease," Circulation, 100:1253-1258, (1999).

(56) References Cited

OTHER PUBLICATIONS

La Scala et al., "The effect of fatty acid composition on the acrylation kinetics of epoxidized triacylglycerols," Journal of the American Oil Chemists' Society, 79(1):59-63, (2002).

Lapidot et al., "Stable Chloroplast Transformation of the Unicellular Red Alga Porphyridium Species," Plant Physiol, 129:7-12, (2002).

Larson et al., "Acyl CoA profiles of transgenic plants that accumulate medium-chain fatty acids indicate inefficient storage lipid synthesis in developing oilseeds," The Plant Journal, 32(4):519-527, (2002).

Leema et al., "Heterotrophic Production of Lutein and Biomass by Chlorella Vulgaris with Different Nitrogen Sources," Algae Biofuel, Studium Press (India) Pvt. Ltd., pp. 91-101, (2011).

Li et al., "Large-scale biodiesel production from microalga Chlorella protothecoides through heterotrophic cultivation in bioreactors," Biotechnology and Bioengineering, 98(04):764-771, (2007).

Li et al., "Broad-spectrum oil-production yeast carbon filter," China Biotechnology, 25(12):39-44(2005), and machine translation.

Li et al., "High-density cultivation of oleaginous yeast Rhodosporidium toruloides Y4 in fed-batch culture," Enzyme and Microbial Technology, 41:312-317, (2007).

Li et al., "Isolation and Purification of Lutein from the Microalga Chlorella vulgaris by Extraction after Saponification," J. Agric. Food Chem., 50(5):1070-1072, (2002).

Li et al., "Perspectives of microbial oils for biodiesel production," Appl Microbiol Biotechnol., 80(5):749-756, (2008).

Lindley, "The impact of food processing antioxidants in vegetable oils, fruits, and vegetables," Trends in Food Science & Technology. 9:336-340, (1998).

List et al., "Melting properties of some structured lipids native to high stearic acid soybean oil," Grasas y Aceites, 55(Fasc. 2):135-137, (2004).

Lubitz, "The Protein Quality, Digestibility, and Composition of Algae, Chlorella 71105," J. Food Sci. 28(2):229-232 (1963).

Manuell et al., "Robust expression of a bioactive mammalian protein in Chlamydomonas chloroplast," Plant Biotech J, 5(3):402-412, (2007).

Mayfield et al., "Expression and Assembly of a Fully Active Antibody in Algae," Proc Natl Acad Sci, 100(2):438-442, (2003).

Meesters et al., "High-cell-density cultivation of the lipid accumulating yeast Cryptococcus curvatus using glycerol as a carbon source," Applied Microbiology and Biotechnology, 45:575-579, (1996).

Mendes et al., "Supercritical Carbon Dioxide Extraction of Compounds With Pharmaceutical Importance from Microalgae," Inorganica Chimica Acta, 356:328-334, (2003).

Meng et al., "Biodiesel production from oleaginous microorganisms," Renewable Energy, 34:1-5, (2009).

Metzger et al., "Botryococcus braunii: A Rich Source for Hydrocarbons and Related Ether Lipids," Applied Microbiology and Biotechnology, 66(5):486-496, (2005).

Miao et al., "Biodiesel Production From Heterotrophic Microalgal Oil," Biosource Technology, 97(06):841-846, (2006).

Miao et al., "High Yield Bio-Oil Production from Fast Pyrolysis by Metabolic Controlling of Chlorella Protothecoides," J. Biotech., 110:85-93, (2004).

Minowa et al., "Oil Production from Algal Cells of Dunaliella tertiolecta by Direct Thermochemical Liquefaction," Fuel, 74(12)1735-1738, (1995).

Mitra et al., "A Chlorella Virus Gene Promoter Functions as a Strong Promoter Both in Plants and Bacteria," Biochemical and Biophysical Research Communications, 204(1):189-194, (1994).

Mitra et al., "The Chlorella Virus Adenine Methyltransferase Gene Promoter is a Strong Promoter in Plants," Plant Molecular Biology, 26(1):85-93, (1994).

Moreno-Perez et al., "Reduced expression of FatA thioesterases in Arabidopsis affects the oil content and fatty acid composition of the seeds," Planta, 235:629-639, (2012).

Morris, "Effect of Growth Temperature on the Cryopreservation of Prototheca," Journal of General Microbiology, 94:395-399, (1976).

Murakami et al., "Lipid Composition of Commercial Bakers' Yeasts Having Different Freeze-tolerance in Frozen Dough," Biosci. Biotechnol. Biochem., 60(11)1874-1876, (1996).

Murakami et al., "Lipids and Fatty Acid Custipvsi lions of Chlorella," Nihon Yuka gakkai-shi, 46(4):423-427, (1997).

Nahm, "Quality Characteristics of West African Shea Butter (Vitellaria Paradoxa) and Approaches to Extend Shelf-Life," Master Thesis, Master of Science in Food Service, Rutgers, the State University of New Jersey, 133 pages, (2011).

Napier et al., "Tailoring plant lipid composition: designer oilseeds come of age," Current Opinion in Plant Biology, 13:330-337, (2010).

Nazaruddin et al., "The Effect of Enzymatic Alcoholysis on the Physicochemical Properties of Commercial Cocoa Butter Substitutes," Pakistan Journal of Nutrition, 10(8):718-723, (2011).

Papanikolaou et al., "Single cell oil production by Yarrowia lipolytica growing on an industrial derivative of animal fat in batch cultures," Appl. Microbiol. Biotechnol., 58:308-312, (2002).

Papanikolaou et al., "Lipid production by Yarrowia lipolytica growing on industrial glycerol in a single-stage continuous culture," Bioresource Technology, 82:43-49, (2002).

Patil et al., "Fatty acid composition of 12 microalgae for possible use in aquaculture feed," Aquacult Int, 15:1-9, (2007).

PCT International Preliminary Report on Patentability (Chapter I) of May 31, 2011 for application PCT/US09/066142.

PCT International Preliminary Report on Patentability (Chapter I) of Aug. 13, 2012 for application PCT/US11/38463.

PCT International Preliminary Report on Patentability (Chapter I) of Dec. 7, 2009 for application PCT/US08/65563.

PCT International Preliminary Report on Patentability for application PCT/US2011/059224 mailed May 16, 2013.

PCT International Search Report and Written Opinion of the International Searching Authority for application PCT/US2013/037261 mailed Aug. 23, 2013.

PCT International Search Report and Written Opinion of the International Searching Authority for application PCT/US2014/035476 mailed Feb. 18, 2015.

PCT International Search Report and Written Opinion of the International Searching Authority for application PCT/US2014/059161 mailed Jun. 1, 2015.

PCT International Search Report and Written Opinion of the International Searching Authority for application PCT/US2015/023181 mailed Jul. 28, 2015.

PCT International Search Report for application PCT/US2011/032582 mailed Aug. 9, 2011.

PCT International Search Report for application PCT/US2011/038463 mailed Jan. 18, 2012.

PCT International Search Report for application PCT/US2011/059224 mailed Jun. 27, 2012.

PCT International Search Report for application PCT/US2012/023696 mailed May 23, 2012.

PCT International Search Report for application PCT/US2012/036690 mailed Aug. 30, 2012.

PCT International Search Report of Aug. 20, 2010 for application PCT/US2009/066142.

PCT International Search Report of Nov. 5, 2010 for application PCT/US2009/066141.

PCT International Search Report of Nov. 6, 2008 for application PCT/US2008/065563.

PCT Invitation to Pay Additional Fees for application PCT/US2014/059161 mailed Mar. 9, 2015.

PCT Invitation to Pay Additional Fees from the International Searching Authority for application PCT/US2014/035476 mailed Dec. 1, 2014.

PCT Written Opinion of the International Search Authority of Aug. 20, 2010 for application PCT/US2009/066142.

PCT Written Opinion of the International Searching Authority for application PCT/US2011/032582 mailed Aug. 9, 2011.

PCT Written Opinion of the International Searching Authority for application PCT/US2011/038463 mailed Jan. 18, 2012.

PCT Written Opinion of the International Searching Authority for application PCT/US2012/023696 mailed May 23, 2012.

PCT Written Opinion of the International Searching Authority for application PCT/US2012/036690 mailed Aug. 30, 2012.

(56) References Cited

OTHER PUBLICATIONS

PCT Written Opinion of the International Searching Authority of Nov. 5, 2010 for application PCT/US2009/066141.
PCT Written Opinion of the International Searching Authority of Nov. 6, 2008 for application PCT/US2008/065563.
Petkov et al., "Which are fatty acids of the green alga Chlorella?," Biochemical Systematics and Ecology, 35:281-285, (2007).
Phippen et al., "Total seed oil and fatty acid methyl ester contents of Cuphea accessions," Industrial Crops and Products, 24:52-59, (2006).
Powell et al., "Algae Feeding in Humans," J. Nutrition, 75:7-12, (1961).
Pratoomyot et al., "Fatty acids composition of 10 microalgal species," Songklanakarin J. Sci. Technol., 27(6):1179-1187, (2005).
Proschold et al., "Portrait of a Species: Chlamydomonas reinhardtii," Genetics, 170(4):1601-1610, (2005).
Qingyu et al., "Fine Cell Structure and Biochemical Compositions of Chlorella Protothecoides after Transferring from Autotrophic to Heterotrophic Metabolish," Journal of Nanjing Univeristy, Natural Sciences Edition, 29(4):622-630, (1993). Abstract.
Radakovets et al., "Genetic Engineering of Algae for Enhanced Biofuel Production," Eukaryotic Cell, 9(04):486-501, (2010).
Radmer et al., "Commercial applications of algae: opportunities and constraints," Journal of Applied Phycology, 6:93-98, (1994).
Randolph-Anderson et al., "Further characterization of the respiratory deficient dum-1 mutation of Chlamydomonas reinhardtii and its use as a recipient for mitochondrial transformation," Mol Gen Genet, 236(2-3):235-244, (1993).
Ratledge, "Regulation of lipid accumulation in oleaginous microorganisms," Biochem Soc Trans., 30(Pt 6):1047-1050, (2002).
Roessler et al., "Genetic Engineering Approaches for Enhanced Production of Biodiesel Fuel from Microalgae," Enzymatic Conversion of Biomass for Fuels Production, Chapter 13, American Chemical Society, doi: 10.1021/bk-1994-0566.ch013, pp. 255-270, (1994).
Rosenberg et al., "A Green Light for Engineered Algae: Redirecting Metabolism to Fuel a Biotechnology Revolution," Current Opinion in Biotechnology. Tissue, Cell and Pathyway Engineering, E-Pub 19:430-436, (2008).
Roy et al., "Production of Intracellular Fat by the Yeast Lipomyces starkeyi," Indian Journal of Experimental Biology, 16(4):511-512, (1978).
Ruiz et al., "Lipids accumulation in Chlorella protothecoides through mixotrophic and heterotrophic cultures for biodiesel production," New Biotechnology, 255:S266-S266, (2009).
Running et al., "Extracellular production of L-ascorbic acid by Chlorella protothecoides, *Prototheca* species, and mutants of P. moriformis during aerobic culturing at low pH," Journal of Industrial Microbiology & Biotechnology, 29:93-98, (2002).
Sakuradani, "Studies of Metabolic Engineering of Useful Lipid-producing Microorganisms," NISR Research Grant, (2004).
Sanchez et al., "Mixotrophic culture of Chlorella pyrenoidosa with olive-mill wastewater as the nutrient medium," Journal of Applied Phycology, 13:443-449, (2001).
Sawayama et al., "Possibility of renewable energy production and CO2 mitigation by thermochemical liquefaction of microalgae," Biomass and Bioenergy, 17(1):33-39, (1999).
Schreier et al., "The use of nuclear-encoded sequences to direct the light-regulated synthesis and transport of a foreign protein into plant chloroplasts," EMBO J, 4(1):25-32, (1985).
Shao et al., "Cloning and expression of metallothionein mutant α-KKS-α in *Anabaena* sp. PCC 7120," Marine Pollution Bulletin, 45(1012):163-167, (2002).
Shi et al., "High-Yield Production of Lutein by the Green Microalga Chlorella protothecoides in Heterotrophic Fed-Batch Culture," Biotechnol. Prog., 18(4):723-727 (2002).
Shi et al., "Production and rapid extraction of lutein and the other lipid-soluble pigments from Chlorella protothecoides grown under heterotrophic and mixotrophic conditions," Nahrung, 43:109-113, (1999).
Smith et al., "Production of hydroxy fatty acids in the seeds of Arabidopsis thaliana," Biochemical Society Transactions, 28(6):947-950, (2000).
Sorger et al., "Triacylglycerol biosynthesis in yeast," Appl. Microbiol Biotechnol, 61:289-299.
Spolaore et al., "Commercial Applications of Microalgae," J. Biosci. Bioeng. 101(2):87-96 (2006).
Sud et al., "Lipid Composition and Sensitivity of Prototheca wickerhamii to Membrane-Active Antimicrobial Agents," Antimicrobial Agents and Chemotherapy, 16:486-490, (1979).
Suda, et al., "Evidence for a novel Chlorella virus-encoded alginate lyase," FEMS Microbiology Letters, 180(1):45-53, (1999).
Suh et al., "What limits production of unusual monoenoic fatty acids in transgenic plants?," Planta, 215:584-595, (2002).
Sun et al, "Characterization of two chitinase genes and one chitosanase gene encoded by Chlorella virus PBCV-1," Virology, 263(2):376-387, (1999).
Sung et al., "The research on the lipid content and composition of microalgae and their impact factors," Marine Science, 12(33)122-128, (2009). (English translation of first two pages).
Swern et al. "Fractionation of tallow fatty acids:Preparation of purified oleic acid and an inedible olive oil substitute," Oil & Soap, 22(11):302-304 (1945).
Szabo et al., "Safety evaluation of a high lipid Whole Algalin Flour (WAF) from Chlorella protothecoides," Regulatory Toxicology and Pharmacology, 63:155-165, (2012).
Szabo et al., "Safety evaluation of Whole Algalin Protein (WAP) from Chlorella protothecoides," Food and Chemical Toxicology, 59:34-45, (2013).
Takeno et al., "Establishment of an overall transformation system for an oil-producing filamentous fungus, ungus, Mortierella alpine 1S-4," Appl Microbiol Biotechnol, 65:419-425, (2004).
Talbot et al., "Formulation and Production of Confectionery Fats," OFI Middle East 2007 Conference and Exhibition, 378 pages, (2007).
Tan et al., "Fatty acid production by heterotrophic Chlorella saccharophila," Hydrobiologia, 215:13-19, (1991).
Tang et al., "Insertion mutagenesis of Chlamydomonas reinhardtii by electroporation and heterologous DNA," Biochem Mol Biol Int, 36(5):1025-1035, (1995).
Tornabene et al., "Lipid composition of the nitrogen starved green alga Neochioris oleoabundans," Enzyme Microb. Technol., 5:435-440, (1983).
U.S. Appl. No. 12/131,766, Advisory Action mailed Oct. 13, 2011.
U.S. Appl. No. 12/131,766, Non-Final Office Action mailed Aug. 1, 2011.
U.S. Appl. No. 12/131,766, Non-Final Office Action mailed Nov. 23, 2010.
U.S. Appl. No. 12/131,766, Non-Final Office Action mailed Dec. 10, 2009.
U.S. Appl. No. 12/131,766, Requirement for Restriction/Election mailed Aug. 5, 2009.
U.S. Appl. No. 12/131,766, Requirement for Restriction/Election mailed Aug. 17, 2010.
U.S. Appl. No. 12/131,773, Advisory Action mailed Jan. 27, 2014.
U.S. Appl. No. 12/131,773, Final Office Action mailed Mar. 21, 2011.
U.S. Appl. No. 12/131,773, Final Office Action mailed Oct. 15, 2013.
U.S. Appl. No. 12/131,773, Non-Final Office Action mailed Jun. 5, 2013.
U.S. Appl. No. 12/131,773, Non-Final Office Action mailed Jun. 25, 2010.
U.S. Appl. No. 12/131,773, Non-Final Office Action mailed Dec. 15, 2009.
U.S. Appl. No. 12/131,773, Notice of Allowance and Examiner Initiated Interview Summary mailed Apr. 1, 2014.
U.S. Appl. No. 12/131,773, Requirement for Restriction/Election mailed Aug. 6, 2009.
U.S. Appl. No. 12/131,783, Final Office Action mailed Jan. 12, 2012.
U.S. Appl. No. 12/131,783, Final Office Action mailed Dec. 13, 2013.
U.S. Appl. No. 12/131,783, Non-Final Office Action mailed Jun. 6, 2011.
U.S. Appl. No. 12/131,783, Non-Final Office Action mailed Jul. 18, 2013.

(56) References Cited

OTHER PUBLICATIONS

U.S. Appl. No. 12/131,783, Notice of Allowance and Examiner Initiated Interview Summary mailed Mar. 24, 2014.
U.S. Appl. No. 12/131,783, Requirement for Restriction/Election mailed Apr. 19, 2011.
U.S. Appl. No. 12/131,793, Non-Final Office Action mailed Nov. 13, 2012.
U.S. Appl. No. 12/131,793, Notice of Allowance mailed Apr. 3, 2013.
U.S. Appl. No. 12/131,804, Final Office Action mailed Feb. 2, 2011.
U.S. Appl. No. 12/131,804, Non-Final Office Action mailed Oct. 26, 2012.
U.S. Appl. No. 12/131,804, Non-Final Office Action mailed Mar. 3, 2010.
U.S. Appl. No. 12/131,804, Non-Final Office Action mailed Jun. 7, 2012.
U.S. Appl. No. 12/131,804, Requirement for Restriction/Election mailed Sep. 17, 2009.
U.S. Appl. No. 12/131,804, Requirement for Restriction/Election mailed Nov. 18, 2009.
U.S. Appl. No. 12/194,389, Final Office Action mailed Jan. 5, 2011.
U.S. Appl. No. 12/194,389, Non-Final Office Action mailed Feb. 4, 2010.
U.S. Appl. No. 12/194,389, Notice of Allowance mailed Jan. 15, 2014.
U.S. Application No. 12/194,389, Requirement for Restriction/Election mailed Oct. 5, 2010.
U.S. Appl. No. 12/194,389, Requirement for Restriction/Election mailed Nov. 2, 2009.
U.S. Appl. No. 12/628,140, Final Office Action mailed Mar. 15, 2013.
U.S. Appl. No. 12/628,140, Final Office Action mailed May 22, 2014.
U.S. Appl. No. 12/628,140, Final Office Action mailed Sep. 12, 2013.
U.S. Appl. No. 12/628,140, Final Office Action mailed Oct. 8, 2014.
U.S. Appl. No. 12/628,140, Non-Final Office Action mailed Jul. 17, 2015.
U.S. Appl. No. 12/628,140, Non-Final Office Action mailed Oct. 30, 2012.
U.S. Appl. No. 12/628,144, Final Office Action mailed Nov. 16, 2010.
U.S. Appl. No. 12/628,144, Final Office Action mailed Dec. 5, 2011.
U.S. Appl. No. 12/628,144, Final Office Action mailed Dec. 12, 2014.
U.S. Appl. No. 12/628,144, Non-Final Office Action mailed May 16, 2014.
U.S. Appl. No. 12/628,144, Non-Final Office Action mailed Jun. 7, 2011.
U.S. Appl. No. 12/628,144, Non-Final Office Action mailed Jul. 8, 2010.
U.S. Appl. No. 12/628,144, Requirement for Restriction/Election and Examiner Initiated Interview Summary mailed Oct. 7, 2014.
U.S. Appl. No. 12/628,149, Non-Final Office Action mailed Jun. 25, 2010.
U.S. Appl. No. 12/628,149, Non-Final Office Action mailed Sep. 16, 2010.
U.S. Appl. No. 12/628,149, Notice of Allowance mailed Dec. 15, 2010.
U.S. Appl. No. 12/628,150, Non-Final Office Action mailed Apr. 29, 2010.
U.S. Appl. No. 12/628,150, Non-Final Office Action mailed Oct. 13, 2010.
U.S. Appl. No. 12/628,150, Notice of Allowance mailed Mar. 21, 2011.
U.S. Appl. No. 12/642,487, Final Office Action mailed Jan. 30, 2014.
U.S. Appl. No. 12/642,487, Non-Final Office Action mailed Jan. 4, 2013.
U.S. Appl. No. 12/642,487, Requirement for Restriction/Election mailed Jun. 18, 2012.
U.S. Appl. No. 12/642,487, Requirement for Restriction/Election mailed Nov. 8, 2012.
U.S. Appl. No. 12/772,164, Final Office Action mailed May 24, 2012.
U.S. Appl. No. 12/772,164, Non-Final Office Action mailed Oct. 12, 2011.
U.S. Appl. No. 12/772,164, Requirement for Restriction/Election mailed Jul. 20, 2011.
U.S. Appl. No. 12/772,170, Final Office Action mailed Feb. 21, 2012.
U.S. Appl. No. 12/772,170, Non-Final Office Action mailed Sep. 13, 2011.
U.S. Appl. No. 12/772,170, Non-Final Office Action mailed Dec. 17, 2013.
U.S. Appl. No. 12/772,170, Notice of Allowance and Examiner-Initiated Interview Summary mailed Jul. 11, 2014.
U.S. Appl. No. 12/772,170, Requirement for Restriction/Election mailed Jul. 13, 2011.
U.S. Appl. No. 12/960,388, Notice of Allowance mailed May 28, 2013.
U.S. Appl. No. 12/960,388, Requirement for Restriction/Election mailed Apr. 1, 2013.
U.S. Appl. No. 12/981,409, Non-Final Office Action mailed Jan. 6, 2012.
U.S. Appl. No. 12/981,409, Notice of Allowance mailed May 29, 2012.
U.S. Appl. No. 12/981,409, Requirement for Restriction/Election mailed Apr. 19, 2012.
U.S. Appl. No. 12/981,409, Requirement for Restriction/Election mailed Oct. 28, 2011.
U.S. Appl. No. 13/029,061, Requirement for Restriction/Election mailed Nov. 29, 2011.
U.S. Appl. No. 13/045,500, Non-Final Office Action mailed Mar. 9, 2012.
U.S. Appl. No. 13/045,500, Non-Final Office Action mailed Jun. 5, 2014.
U.S. Appl. No. 13/045,500, Final Office Action mailed Sep. 26, 2012.
U.S. Appl. No. 13/073,757, Non-Final Office Action mailed Aug. 15, 2011.
U.S. Appl. No. 13/073,757, Non-Final Office Action mailed Dec. 29, 2011.
U.S. Appl. No. 13/073,757, Notice of Allowance mailed Apr. 17, 2012.
U.S. Appl. No. 13/087,311, Final Office Action mailed Dec. 16, 2013.
U.S. Appl. No. 13/087,311, Non-Final Office Action mailed Apr. 23, 2013.
U.S. Appl. No. 13/087,311, Non-Final Office Action mailed Jun. 24, 2014.
U.S. Appl. No. 13/118,365, Final Office Action mailed Jul. 22, 2013.
U.S. Appl. No. 13/118,365, Non-Final Office Action mailed Feb. 11, 2013.
U.S. Appl. No. 13/118,365, Requirement for Restriction/Election mailed Oct. 11, 2012.
U.S. Appl. No. 13/273,179, Non-Final Office Action mailed Jan. 28, 2014.
U.S. Appl. No. 13/273,179, Notice of Allowance mailed Jul. 11, 2014.
U.S. Appl. No. 13/273,179, Requirement for Restriction/Election mailed Nov. 14, 2013.
U.S. Appl. No. 13/288,815, Final Office Action mailed Oct. 22, 2014.
U.S. Appl. No. 13/288,815, Non-Final Office Action mailed Jun. 18, 2014.
U.S. Appl. No. 13/288,815, Notice of Allowance mailed Feb. 26, 2015.
U.S. Appl. No. 13/288,815, Requirement for Restriction/Election mailed Jan. 30, 2014.
U.S. Appl. No. 13/365,253, Requirement for Restriction/Election mailed Dec. 16, 2014.
U.S. Appl. No. 13/406,417, Non-Final Office Action mailed Nov. 5, 2012.
U.S. Appl. No. 13/406,417, Requirement for Restriction/Election mailed Apr. 30, 2012.
U.S. Appl. No. 13/464,948, Requirement for Restriction/Election mailed Aug. 21, 2013.
U.S. Appl. No. 13/479,194, Non-Final Office Action mailed Mar. 26, 2014.
U.S. Appl. No. 13/479,200, Non-Final Office Action mailed Apr. 10, 2013.
U.S. Appl. No. 13/479,200, Non-Final Office Action mailed Sep. 9, 2013.

(56) References Cited

OTHER PUBLICATIONS

U.S. Appl. No. 13/479,200, Notice of Allowance mailed Nov. 25, 2013.
U.S. Appl. No. 13/479,200, Requirement for Restriction/Election mailed Jan. 15, 2013.
U.S. Appl. No. 13/527,480, Final Office Action mailed Jan. 16, 2014.
U.S. Appl. No. 13/527,480, Non-Final Office Action mailed Jun. 26, 2013.
U.S. Appl. No. 13/527,480, Requirement for Restriction/Election mailed May 3, 2013.
U.S. Appl. No. 13/543,666, Non-Final Office Action mailed Sep. 5, 2013.
U.S. Appl. No. 13/543,666, Notice of Allowance mailed Feb. 10, 2014.
U.S. Appl. No. 13/543,666, Requirement for Restriction/Election mailed Jan. 3, 2013.
U.S. Appl. No. 13/547,457, Final Office Action mailed Mar. 20, 2014.
U.S. Appl. No. 13/547,457, Non-Final Office Action mailed Jul. 8, 2013.
U.S. Appl. No. 13/547,457, Notice of Allowance and Examiner-Initiated Interview Summary mailed May 29, 2014.
U.S. Appl. No. 13/550,412, Non-Final Office Action mailed Oct. 29, 2012.
U.S. Appl. No. 13/550,412, Notice of Allowance mailed Feb. 21, 2013.
U.S. Appl. No. 13/555,009, Non-Final Office Action mailed Sep. 16, 2014.
U.S. Appl. No. 13/555,009, Notice of Allowance mailed Jan. 9, 2015.
U.S. Appl. No. 13/555,009, Requirement for Restriction/Election mailed Jun. 16, 2014.
U.S. Appl. No. 13/558,252, Final Office Action mailed Jul. 9, 2013.
U.S. Appl. No. 13/558,252, Non-Final Office Action mailed Jan. 18, 2013.
U.S. Appl. No. 13/558,252, Notice of Allowance mailed Oct. 23, 2013.
U.S. Appl. No. 13/601,928, Non-Final Office Action mailed Jan. 31, 2013.
U.S. Appl. No. 13/601,928, Notice of Allowance mailed Feb. 26, 2013.
U.S. Appl. No. 13/601,937, Final Office Action mailed Nov. 22, 2013.
U.S. Appl. No. 13/601,937, Non-Final Office Action mailed Jun. 10, 2013.
U.S. Appl. No. 13/601,937, Requirement for Restriction/Election mailed Feb. 27, 2013.
U.S. Appl. No. 13/630,757, Non-Final Office Action mailed Apr. 23, 2015.
U.S. Appl. No. 13/630,767, Non-Final Office Action mailed Oct. 27, 2014.
U.S. Appl. No. 13/630,757, Requirement for Restriction/Election mailed Jun. 12, 2014.
U.S. Appl. No. 13/650,018, Non-Final Office Action mailed Dec. 23, 2013.
U.S. Appl. No. 13/650,018, Notice of Allowance mailed Apr. 1, 2015.
U.S. Appl. No. 13/650,018, Notice of Allowance mailed Apr. 10, 2015.
U.S. Appl. No. 13/650,018, Notice of Allowance mailed Aug. 14, 2014.
U.S. Appl. No. 13/650,018, Requirement for Restriction/Election mailed Aug. 22, 2013.
U.S. Appl. No. 13/650,024, Non-Final Office Action mailed Jul. 2, 2013.
U.S. Appl. No. 13/650,024, Notice of Allowance mailed Oct. 17, 2013.
U.S. Appl. No. 13/804,185, Non-Final Office Action mailed Jun. 1, 2015.
U.S. Appl. No. 13/804,185, Requirement for Restriction/Election mailed Mar. 16, 2015.
U.S. Appl. No. 13/849,330, Requirement for Restriction/Election mailed Jan. 21, 2015.
U.S. Appl. No. 13/852,116, Final Office Action mailed Aug. 18, 2014.
U.S. Appl. No. 13/852,116, Non-Final Office Action mailed Mar. 26, 2014.
U.S. Appl. No. 13/852,116, Notice of Allowance mailed Nov. 7, 2014.
U.S. Appl. No. 13/865,974, Non-Final Office Action mailed May 2, 2014.
U.S. Appl. No. 13/865,974, Notice of Allowance mailed Oct. 22, 2014.
U.S. Appl. No. 13/865,974, Requirement for Restriction/Election mailed Jan. 29, 2014.
U.S. Appl. No. 13/889,214, Non-Final Office Action mailed Sep. 18, 2013.
U.S. Appl. No. 13/889,214, Notice of Allowance mailed Apr. 28, 2014.
U.S. Appl. No. 13/889,221, Non-Final Office Action mailed Sep. 6, 2013.
U.S. Appl. No. 13/889,221, Notice of Allowance mailed Apr. 24, 2014.
U.S. Appl. No. 13/941,342, Notice of Allowance mailed Jul. 24, 2015.
U.S. Appl. No. 13/941,342, Requirement for Restriction/Election mailed Apr. 13, 2015.
U.S. Appl. No. 13/941,346, Final Office Action mailed Jun. 26, 2014.
U.S. Appl. No. 13/941,346, Non-Final Office Action mailed Jan. 21, 2014.
U.S. Appl. No. 13/941,346, Non-Final Office Action mailed Nov. 3, 2014.
U.S. Appl. No. 13/941,346, Notice of Allowance mailed Feb. 23, 2015.
U.S. Appl. No. 13/941,357, Final Office Action mailed Nov. 6, 2014.
U.S. Appl. No. 13/941,357, Non-Final Office Action mailed Jun. 3, 2014.
U.S. Appl. No. 13/941,357, Notice of Allowance mailed Mar. 30, 2015.
U.S. Appl. No. 13/941,357, Requirement for Restriction/Election mailed Jan. 7, 2014.
U.S. Appl. No. 14/184,288, Requirement for Restriction/Election mailed Jun. 9, 2015.
U.S. Appl. No. 14/262,070, Non-Final Office Action mailed Jul. 10, 2015.
U.S. Appl. No. 14/276,943, Requirement for Restriction/Election mailed Jun. 4, 2015.
Ueno et al., "Optimization of heterotrophic culture conditions for n-alkane utilization and phylogenetic position based on the 18S rDNA sequence of a thermotolerant Prototheca zopfii strain," J Biosci Bioeng, 94(2):160-165, (2002). Abstract. [Retrieved from the Internet Dec. 1, 2014: <URL: http://www.ncbi.nlm.nih.gov/pubmed/16233286>].
Urano, et al., "Effect of Osmotic Stabilizers on Protoplast Generation of Chlorella ellipsoidea Yellow/White Color Mutants," Journal of Bioscience and Bioengineering, 90(5):567-569, (2000).
Van Etten et al., "Giant viruses infecting algae," Annu Rev Microbiol, 53:447-494, (1999).
Vazquez-Bermudez et al., "Carbon Supply and 2-Oxoglutarate Effects on Expression of Nitrate Reductase and Nitrogen-Regulated Genes in *Synechococcus* sp. strain PCC 7942," FEMS Microbiology Letters, 221(2)155-159, (2003).
Vazquez-Bermudez et al., "Uptake of 2-Oxoglutarate in Synechococcus Strains Transformed with the *Escherichia coli* kgtP Gene," Journal of Bacteriology, 182(1):211-215, (2000).
Walker et al., "Characterization of the Dunaliella tertiolecta RbcS Genes and Their Promoter Activity in Chlamydomonas reinhardtii," Plant Cell Rep, 23(10-11):727-735, (2005).
Warner et al., "Analysis of Tocopherols and Phytosterols in Vegetable Oils by HPLC with Evaporative Light-Scattering Detection," JAOCS, 67(11):827-831 (1990).
Westphal, et al., "Vipp1 Deletion Mutant of Synechocystis: A Connection Between Bacterial Phage Shock and Thylakoid Biogenesis," Proc Natl Acad Sci U S A., 98(7):4243-4248, (2001).

(56) References Cited

OTHER PUBLICATIONS

Wiberg et al., "The distribution of caprylate, caprate and laurate in lipids from developing and mature seeds of transgenic *Brassica napus* L.," Planta, 212:33-40, (2000).

Wu et al., "A Comparative Study of Gases Generated from Simulant Thermal Degradation of Autotrophic and Heterotrophic Chlorella," Progress in Natural Science, 2(4):311-318, (1992).

Wu et al, "Comparative study on Liposoluble Compounds in Autotrophic and Heterotrophic Chlorella Protothecoides," Acta Botanica Sinica, 35(11):849-858, (1992).

Wu et al., "New Discoveries in Study on Hydrocarbons From Thermal Degradation of Heterotrophically Yellowing Algae," Science in China, 37(3):326-35, (1994).

Xiong et al., "High-density fermentation of microalga Chlorella protothecoides in bioreactor for microbio-diesel production," Appl. Microbiol. Biotechnol., 78:29-36, (2008).

Xu et al., "High quality biodiesel production from a microalga Chlorella protothecoides by heterotrophic growth in fermenters," Journal of Biotechnology, 126:499-507, (2006).

Yamada et al., "Alternative expression of a chitosanase gene produces two different proteins in cells infected with Chlorella virus CVK2," Virology, 230(2):361-368, (1997).

Yamada et al., "Chlorella viruses," Adv Virus Res, 66:293-336, (2006).

Yu et al., "Modifications of the metabolic pathways of lipid and triacylglycerol production in microalgae," Microbial Cell Factories, 10:91, (2011). [Retrieved from the Internet Jul. 24, 2012: <URL: http://www.microbialcellfactories.com/content/10/1/91>].

Zaidul et al., "Supercritical carbon dioxide (SC-0O2) extraction and fractionation of palm kernel oil from palm kernel as cocoa butter replacers blend," Journal of Food Engineering, 73:210-216, (2006).

Zhang et al., "Malic enzyme: the controlling activity for lipid production? Overexpression of malic enzyme in Mucor circinelloides leads to a 2.5-fold increase in lipid accumulation," Microbiology, 153(7):2013-2025, (2007).

Zhao et al., "Medium optimization for lipid production through co-fermentation of glucose and xylose by the oleaginous yeast Lipomyces starkeyi," Eur. J. Lipid Sci. Technol., 110:405-412, (2008).

Zurawski et al., "Nucleotide sequence of the gene for the Mr 32,000 thylakoid membrane protein from Spinacia oleracea and Nicotiana debneyi predicts a totally conserved primary translation product of Mr 38,950," Proc Natl Acad Sci, 79(24):7699-7703, (1982).

EPO Supplementary European Search Report and European Search Opinion for application EP12741997.6 mailed Aug. 31, 2015.

Huss et al., "Deoxyribonucleic acid reassociation in the taxonomy of the genus *Chlorella*," Arch Microbiol, 150:509-511, (1988).

Kerton et al., "Alternative Solvents for Green Chemistry," RSC Publishing, 238 pages, (2009).

PCT Invitation to Pay Additional Fees for application PCT/US2015/039951 mailed Nov. 20, 2015.

U.S. Appl. No. 13/365,253, Notice of Allowance mailed Sep. 24, 2015.

U.S. Appl. No. 13/630,757, Notice of Allowance mailed Oct. 23, 2015.

U.S. Appl. No. 13/804,185, Final Office Action mailed Dec. 11, 2015.

U.S. Appl. No. 14/184,288, Non-Final Office Action mailed Sep. 11, 2015.

U.S. Appl. No. 14/262,070, Notice of Allowance mailed Oct. 20, 2015.

U.S. Appl. No. 14/276,943, Notice of Allowance mailed Sep. 22, 2015.

Day et al., "An investigation of the heterotrophic culture of the green alga Tetraselmis," Journal of Applied Phycology, 8:73-77, (1996).

EPO Supplementary European Search Report and European Search Opinion for application EP13778920.2 (EP13778920) mailed Jan. 25, 2016.

U.S. Appl. No. 14/474,238, Non-Final Office Action mailed Feb. 2, 2016.

U.S. Appl. No. 12/628,140, Final Office Action mailed Feb. 2, 2016.

* cited by examiner

SEQUENCE LISTING

<160> NUMBER OF SEQ ID NOS: 1

<210> SEQ ID NO 1
<211> LENGTH: 8660
<212> TYPE: DNA
<213> ORGANISM: Artificial Sequence
<220> FEATURE:
<223> OTHER INFORMATION: Synthesized

<400> SEQUENCE: 1

```
cactggcagc agccactggt aacaggatta gcagagcgag gtatgtaggc ggtgctacag      60
agttcttgaa gtggtggcct aactacggct acactagaag gacagtattt ggtatctgcg     120
ctctgctgaa gccagttacc ttcggaaaaa gagttggtag ctcttgatcc ggcaaacaaa     180
ccaccgctgg tagcggtggt ttttttgttt gcaagcagca gattacgcgc agaaaaaaag     240
gatctcaaga agatcctttg atcttttcta cggggtctga cgctcagtgg aacgaaaact     300
cacgttaagg gattttggtc atgagattat caaaaaggat cttcacctag atccttttaa     360
attaaaaatg aagttttaaa tcaatctaaa gtatatatga gtaaacttgg tctgacagtt     420
accaatgctt aatcagtgag gcacctatct cagcgatctg tctatttcgt tcatccatag     480
ttgcctgact ccccgtcgtg tagataacta cgatacggga gggcttacca tctggcccca     540
gtgctgcaat gataccgcga gacccacgct caccggctcc agatttatca gcaataaacc     600
agccagccgg aagggccgag cgcagaagtg gtcctgcaac tttatccgcc tccatccagt     660
ctattaattg ttgccgggaa gctagagtaa gtagttcgcc agttaatagt ttgcgcaacg     720
ttgttgccat tgctacaggc atcgtggtgt cacgctcgtc gtttggtatg gcttcattca     780
gctccggttc ccaacgatca aggcgagtta catgatcccc catgttgtgc aaaaaagcgg     840
ttagctcctt cggtcctccg atcgttgtca gaagtaagtt ggccgcagtg ttatcactca     900
tggttatggc agcactgcat aattctctta ctgtcatgcc atccgtaaga tgcttttctg     960
tgactggtga gtactcaacc aagtcattct gagaatagtg tatgcggcga ccgagttgct    1020
cttgcccggc gtcaatacgg gataataccg cgccacatag cagaacttta aaagtgctca    1080
```

```
tcattggaaa acgttcttcg gggcgaaaac tctcaaggat cttaccgctg ttgagatcca    1140
gttcgatgta acccactcgt gcacccaact gatcttcagc atcttttact ttcaccagcg    1200
tttctgggtg agcaaaaaca ggaaggcaaa atgccgcaaa aaagggaata agggcgacac    1260
ggaaatgttg aatactcata ctcttccttt ttcaatatta ttgaagcatt tatcagggtt    1320
attgtctcat gagcggatac atatttgaat gtatttagaa aaataaacaa atagggttc     1380 cgcgcacatt tccccgaaaa gtgccacctg acgtctaaga aaccattatt atcatgacat    1440
taacctataa aaataggcgt atcacgaggc cctttcgtct cgcgcgtttc ggtgatgacg    1500
gtgaaaacct ctgacacatg cagctcccgg agacggtcac agcttgtctg taagcggatg    1560
ccgggagcag acaagcccgt cagggcgcgt cagcgggtgt tggcgggtgt cggggctggc    1620
ttaactatgc ggcatcagag cagattgtac tgagagtgca ccatatgcgg tgtgaaatac    1680
cgcacagatg cgtaaggaga aaataccgca tcaggcgcca ttcgccattc aggctgcgca    1740
actgttggga agggcgatcg gtgcgggcct cttcgctatt acgccagctg gcgaaagggg    1800
gatgtgctgc aaggcgatta agttgggtaa cgccagggtt ttcccagtca cgacgttgta    1860
aaacgacggc cagtgaattg atgcatgctc ttccgcctgg agctggtgca gagcatgggg    1920
cagtttgcgg aggagagggt gctccccgtg ctgcaccccg tggacaagct gtggcagccg    1980
caggacttcc tgcccgaccc cgagtcgccc gacttcgagg accaggtggc ggagctgcgc    2040
gcgcgcgcca aggacctgcc cgacgagtac tttgtggtgc tggtgggcga catgatcacg    2100
gaggaggcgc tgccgaccta catggccatg ctcaacacct tggacggtgt gcgcgacgac    2160
acgggcgcgg ctgaccaccc gtgggcgcgc tggacgcggc agtgggtggc cgaggagaac    2220
cggcacggcg acctgctgaa caagtactgt tggctgacgg ggcgcgtcaa catgcgggcc    2280
gtggaggtga ccatcaacaa cctgatcaag agcggcatga cccgcagac ggacaacaac     2340 ccttacttgg gcttcgtcta cacctccttc caggagcgcg ccaccaagta ggtaccctt     2400 cttgcgctat gacacttcca gcaaaaggta gggcgggctg cgagacggct tcccggcgct    2460
gcatgcaaca ccgatgatgc ttcgaccccc cgaagctcct tcggggctgc atgggcgctc    2520
cgatgccgct ccagggcgag cgctgtttaa atagccaggc ccccgattgc aaagacatta    2580
tagcgagcta ccaaagccat attcaaacac ctagatcact accacttcta cacaggccac    2640
tcgagcttgt gatcgcactc cgctaagggg gcgcctcttc ctcttcgttt cagtcacaac    2700
ccgcaaactc tagaatatca atgctgctgc aggccttcct gttcctgctg ccggcttcg     2760 ccgccaagat cagcgcctcc atgacgaacg agacgtccga ccgcccctg gtgcacttca     2820 cccccaacaa gggctggatg aacgaccccca acggcctgtg gtacgacgag aaggacgcca    2880
agtggcacct gtacttccag tacaacccga acgacaccgt ctgggggacg cccttgttct    2940
ggggccacgc cacgtccgac gacctgacca actgggagga ccagcccatc gccatcgccc    3000
cgaagcgcaa cgactccggc gccttctccg gctccatggt ggtggactac aacaacacct    3060
ccggcttctt caacgacacc atcgacccgc gccagcgctg cgtggccatc tggacctaca    3120 acacccccgga gtccgaggag cagtacatct cctacagcct ggacggcggc tacaccttca    3180
ccgagtacca gaagaacccc gtgctggccg ccaactccac ccagttccgc gacccgaagg    3240
tcttctggta cgagccctcc cagaagtgga tcatgaccgc ggccaagtcc caggactaca    3300
agatcgagat ctactcctcc gacgacctga agtcctggaa gctggagtcc gcgttcgcca    3360
acgagggctt cctcggctac cagtacgagt gccccggcct gatcgaggtc cccaccgagc    3420
```

```
aggaccccag caagtcctac tgggtgatgt tcatctccat caaccccggc gccccggccg   3480
gcggctcctt caaccagtac ttcgtcggca gcttcaacgg cacccacttc gaggccttcg   3540
acaaccagtc ccgcgtggtg gacttcggca aggactacta cgccctgcag accttcttca   3600
acaccgaccc gacctacggg agcgccctgg gcatcgcgtg ggcctccaac tgggagtact   3660
ccgccttcgt gcccaccaac ccctggcgct cctccatgtc cctcgtgcgc aagttctccc   3720
tcaacaccga gtaccaggcc aacccggaga cggagctgat caacctgaag gccgagccga   3780
tcctgaacat cagcaacgcc ggcccctgga gccggttcgc caccaacacc acgttgacga   3840
aggccaacag ctacaacgtc gacctgtcca acagcaccgg caccctggag ttcgagctgg   3900
tgtacgccgt caacaccacc cagacgatct ccaagtccgt gttcgcggac ctctccctct   3960
ggttcaaggg cctggaggac cccgaggagt acctccgcat gggcttcgag gtgtccgcgt   4020
cctccttctt cctggaccgc gggaacagca aggtgaagtt cgtgaaggag aaccccctact   4080 tcaccaaccg catgagcgtg aacaaccagc ccttcaagag cgagaacgac ctgtcctact   4140
acaaggtgta cggcttgctg gaccagaaca tcctggagct gtacttcaac gacggcgacg   4200
tcgtgtccac caacacctac ttcatgacca ccgggaacgc cctgggctcc gtgaacatga   4260 cgacggggt ggacaacctg ttctacatcg acaagttcca ggtgcgcgag gtcaagtgac   4320
aattgacgga gcgtcgtgcg ggagggagtg tgccgagcgg ggagtccccgg tctgtgcgag   4380 gcccggcagc tgacgctggc gagccgtacg ccccgagggt cccccctcccc tgcaccctct   4440 tccccttccc tctgacggcc gcgcctgttc ttgcatgttc agcgacggat cccgcgtctc   4500
gaacagagcg cgcagaggaa cgctgaaggt ctcgcctctg tcgcacctca gcgcggcata   4560
caccacaata accacctgac gaatgcgctt ggttcttcgt ccattagcga agcgtccggt   4620
tcacacacgt gccacgttgg cgaggtggca ggtgacaatg atcggtggag ctgatggtcg   4680
aaacgttcac agcctaggga tatcgaattc ggccgacagg acgcgcgtca aggtgctgg   4740 tcgtgtatgc cctggccggc aagtcgttgc tgctgctggt tagtgattcc gcaaccctga   4800 tttttggcgtc ttattttggc gtggcaaacg ctggcgcccg cgagccgggc cggcggcgat   4860
gcggtgcccc acggctgccg gaatccaagg gaggcaagag cgcccgggtc agttgaaggg   4920
ctttacgcgc aaggtacagc cgctcctgca aggctgcgtg gtggaattgg acgtgcaggt   4980
cctgctgaag ttcctccacc gcctcaccag cggacaaagc accggtgtat caggtccgtg   5040
tcatccactc taaagaactc gactacgacc tactgatggc cctagattct tcatcaaaaa   5100
cgcctgagac acttgcccag gattgaaact ccctgaaggg accaccaggg gccctgagtt   5160
gttccttccc cccgtggcga gctgccagcc aggctgtacc tgtgatcgag ctggcggga   5220 aaataggctt cgtgtgctca ggtcatggga ggtgcaggac agctcatgaa acgccaacaa   5280
tcgcacaatt catgtcaagc taatcagcta tttcctcttc acgagctgta attgtcccaa   5340
aattctggtc taccggggt gatccttcgt gtacgggccc ttccctcaac cctaggtatg   5400
cgcgcatgcg gtcgccgcgc aactcgcgcg agggccgagg gtttgggacg gccgtcccg   5460 aaatgcagtt gcacccggat gcgtggcacc ttttttgcga taatttatgc aatggactgc   5520
tctgcaaaat tctggctctg tcgccaaccc taggatcagc ggcgtaggat tcgtaatca   5580 ttcgtcctga tggggagcta ccgactaccc taatatcagc ccgactgcct gacgccagcg   5640
tccacttttg tgcacacatt ccattcgtgc ccaagacatt tcattgtggt gcgaagcgtc   5700
cccagttacg ctcacctgtt tcccgacctc cttactgttc tgtcgacaga gcgggcccac   5760
aggccggtcg cagccactag tatggctatc aagacgaaca ggcagcctgt ggagaagcct   5820
```

```
ccgttcacga tcgggacgct gcgcaaggcc atccccgcgc actgtttcga gcgctcggcg   5880
cttcgtgggc gcgcccccaa ggccaacggc agcgccgtga gcctgaagtc cggcagcctg   5940
aacaccctgg aggaccccc cagcagcccc ccccccgca ccttcctgaa ccagctgccc    6000
gactggagcc gcctgcgcac cgccatcacc accgtgttcg tggccgccga gaagcagttc   6060
acccgcctgg accgcaagag caagcgcccc gacatgctgg tggactggtt cggcagcgag   6120
accatcgtgc aggacggcct ggtgttccgc gagcgcttca gcatccgcag ctacgagatc   6180
ggcgccgacc gcaccgccag catcgagacc ctgatgaacc acctgcagga caccagcctg   6240
aaccactgca agagcgtggg cctgctgaac gacggcttcg gccgcacccc cgagatgtgc   6300
acccgcgacc tgatctgggt gctgaccaag atgcagatcg tggtgaaccg ctaccccacc   6360
tggggcgaca ccgtggagat caacagctgg ttcagccaga gcggcaagat cggcatgggc   6420
cgcgagtggc tgatcagcga ctgcaacacc ggcgagatcc tggtgcgcgc caccagcgcc   6480
tgggccatga tgaaccagaa gacccgccgc ttcagcaagc tgccctgcga ggtgcgccag   6540
gagatcgccc cccacttcgt ggacgccccc ccgtgatcg aggacaacga ccgcaagctg   6600
cacaagttcg acgtgaagac cggcgacagc atctgcaagg gcctgacccc cggctggaac   6660
gacttcgacg tgaaccagca cgtgagcaac gtgaagtaca tcggctggat tctggagagc   6720
atgcccaccg aggtgctgga gacccaggag ctgtgcagcc tgaccctgga gtaccgccgc   6780
gagtgcggcc gcgagagcgt ggtggagagc gtgaccagca tgaaccccag caaggtgggc   6840
gaccgcagcc agtaccagca cctgctgcgc ctggaggacg cgccgacat catgaagggc   6900 cgcaccgagt ggcgccccaa gaacgccggc accaaccgcg ccatcagcac ctgattaatt   6960
aactcgaggc agcagcagct cggatagtat cgacacactc tggacgctgg tcgtgtgatg   7020
gactgttgcc gccacacttg ctgccttgac ctgtgaatat ccctgccgct tttatcaaac   7080
agcctcagtg tgtttgatct tgtgtgtacg cgcttttgcg agttgctagc tgcttgtgct   7140
atttgcgaat accaccccca gcatcccctt ccctcgtttc atatcgcttg catcccaacc   7200
gcaacttatc tacgctgtcc tgctatccct cagcgctgct cctgctcctg ctcactgccc   7260
ctcgcacagc cttggtttgg gctccgcctg tattctcctg gtactgcaac ctgtaaacca   7320
gcactgcaat gctgatgcac gggaagtagt gggatgggaa cacaaatgga aagcttgagc   7380
tccagccacg gcaacaccgc gcgccttgcg gccgagcacg gcgacaagaa cctgagcaag   7440
atctgcgggc tgatcgccag cgacgagggc cggcacgaga tcgcctacac gcgcatcgtg   7500
gacgagttct tccgcctcga ccccgagggc gccgtcgccg cctacgccaa catgatgcgc   7560
aagcagatca ccatgcccgc gcacctcatg gacgacatgg ccacggcga ggccaacccg   7620 ggccgcaacc tcttcgccga cttctccgcg gtcgccgaga agatcgacgt ctacgacgcc   7680
gaggactact gccgcatcct ggagcacctc aacgcgcgct ggaaggtgga cgagcgccag   7740
gtcagcggcc aggccgccgc ggaccaggag tacgtcctgg gcctgcccca gcgcttccgg   7800
aaactcgccg agaagaccgc cgccaagcgc aagcgcgtcg cgcgcaggcc cgtcgccttc   7860
tcctggagaa gagcctctag agtcgacctg caggcatgca agcttggcgt aatcatggtc   7920
atagctgttt cctgtgtgaa attgttatcc gctcacaatt ccacacaaca tacgagccgg   7980
aagcataaag tgtaaagcct ggggtgccta atgagtgagc taactcacat taattgcgtt   8040
gcgctcactg cccgctttcc agtcgggaaa cctgtcgtgc cagctgcatt aatgaatcgg   8100
ccaacgcgcg gggagaggcg gtttgcgtat tgggcgctct tccgcttcct cgctcactga   8160
```

```
ctcgctgcgc tcggtcgttc ggctgcggcg agcggtatca gctcactcaa aggcggtaat      8220
acggttatcc acagaatcag gggataacgc aggaaagaac atgtgagcaa aaggccagca      8280
aaaggccagg aaccgtaaaa aggccgcgtt gctggcgttt ttccataggc tccgcccccc      8340
tgacgagcat cacaaaaatc gacgctcaag tcagaggtgg cgaaacccga caggactata      8400
aagataccag gcgtttcccc ctggaagctc cctcgtgcgc tctcctgttc cgaccctgcc      8460
gcttaccgga tacctgtccg cctttctccc ttcgggaagc gtggcgcttt ctcatagctc      8520
acgctgtagg tatctcagtt cggtgtaggt cgttcgctcc aagctgggct gtgtgcacga      8580 acccccgtt cagcccgacc gctgcgcctt atccggtaac tatcgtcttg agtccaaccc       8640
ggtaagacac gacttatcgc                                                  8660
```

LAURIC ESTER COMPOSITIONS

CROSS REFERENCE TO RELATED APPLICATIONS

This application claims the benefit under 35 U.S.C. 119(e) of U.S. Provisional Patent Application No. 61/972,026, filed Mar. 28, 2014, which is incorporated herein by reference in its entirety for all purposes.

REFERENCE TO A SEQUENCE LISTING

This application includes an electronic sequence listing in a filed named "460107-Sequence.txt", created on Jun. 10, 2015, and containing 10,834 bytes, which is hereby incorporated by reference in its entirety for all purposes.

FIELD

Embodiments of the present invention relate to compositions containing alkyl esters derived from triglyceride oils produced from genetically engineered microalgae. Specific embodiments relate to esters derived from oils with high C10-C12 fatty acid profile. Compositions comprising the esters include cleaning products, completion fluids, workover fluids, drilling fluids, metal working fluids, lubricants, paints, and inks.

BACKGROUND

Monoalkyl esters derived from triglyceride vegetable oils and animal fats find use as environmentally friendly compounds in variety of applications ranging from fuels to solvents. Triglycerides contain fatty acid chains that vary in length, but typically have a fatty acid profile favoring chain lengths of 12, 16, and/or 18 carbons. A fatty acid profile high in lauric acid, a 12 carbon fatty acid, is characteristic of coconut or palm kernel oils. Transesterification of these oils with an alkyl alcohol forms esters rich in laurates. However as noted in U.S. Pat. No. 8,617,317, fatty acid esters such as lauryl methyl esters have unpleasant and potent odors. These disadvantages limit acceptance of their use, particularly in applications with human exposure, for use in areas with inadequate ventilation, and/or where large quantities of the esters are required. Illustrative applications where unpleasant odor is disadvantageous include use as cleaning agents in personal care products such as hand cleaners.

Following drilling and cementing operations in an oil or gas well, a well remediation process is often necessary prior to production of the oil or gas. Drilling fluid employed in the drilling well typically contains viscosifiers and other additives that are necessary for suspending and removing the drill cuttings and for maintaining stability of the well. However these and other unwanted downhole products and deposits can prevent efficient oil/gas production such as by partially occluding the well. Completion fluids having cleaning properties capable of removing these unwanted products are thus highly desirable for maximizing flow of the production oil or gas.

In the use of a cutting or shaping tool on a workpiece, friction between the tool and the workpiece can cause wear on the tool, hinder the cutting, metal forming, or stamping process, lead to slow manufacturing cycles, and negatively affect the quality and finish of the workpiece. Lubricants are typically used to overcome these undesirable effects. In choosing the appropriate lubricants, consideration also needs to be given to the compatibility of the lubricant in the application, whether the lubricant can operate efficiently under the conditions of its use, and the ease with which the lubricant can be removed if necessary. Of further importance is the environmental impact of the lubricant in its use and disposal, and on the health of workers using the lubricant. In this regard, properties such as the biodegradability and VOC (volatile organic compound) content of the lubricant are important considerations.

SUMMARY

In one embodiment, provided is a composition comprising C1-C4 esters of fatty acids derived from oil produced by a microalgae. In some embodiments, the oil has a fatty acid profile of at least 10% C10:0 and 40% C12:0 fatty acids. The esters derived from the microalgal oils having high C10-C12 content are surprisingly found to have a reduced odor compared to the corresponding esters derived from vegetable or animal triglyceride oils with high C12 content. In some embodiments the esters provided herein and/or compositions containing the esters have one or more features of improved odor, faster drying rate, and lower VOC content in comparison to vegetable or animal based esters such as those with at least 40% C12:0 fatty acids. In some embodiments the esters provided herein are unfractionated or and/or are formed from unfractionated natural oils.

In one embodiment, provided is a composition comprising C1-C4 esters of fatty acids derived from oil produced by a microalgae, the oil having a fatty acid profile of at least 10% C10:0 and 40% C12:0 fatty acids, the composition having a reduced odor compared to a composition where all the fatty acids are derived from vegetable or animal triglyceride oil having a fatty acid profile of at least 40% C12:0 fatty acids. In some embodiments, the unpleasant odor associated with the vegetable or animal oil is characteristic of a C6 or C8 fatty acid or ester thereof.

In some embodiments, the C1-C4 ester is a methyl, ethyl, propyl, iso-propyl, butyl, or a tert-butyl ester. In some embodiments, the ester is a methyl ester. In some embodiments, the ester is an ethyl ester. In some embodiments, the ester is an iso-propyl ester.

In some embodiments, the fatty acid profile is characterized wherein C12:0>C10:0>C14:0.

In some embodiments, at least 50% of the fatty acids are C12:0 fatty acids. In some embodiments, at least 60% of the fatty acids are C:10 and C:12 fatty acids.

In some embodiments, at least 15% of the fatty acids are C10:0 fatty acids. In some embodiments, 15-25% of the fatty acids are C10:0 fatty acids.

In some embodiments, 10-15% of the fatty acids are C14:0 fatty acids.

In some embodiments, less than 8%, 7%, or 6% of the fatty acids are C16:0 fatty acids.

In some embodiments, less than 0.5% of the fatty acids are C8:0 fatty acids.

In some embodiments, less than 0.1%, 0.01%, or 0.001% of the fatty acids are C6:0 fatty acids.

In some embodiments, the compositions provided herein comprise sterols from the microalgae, wherein the amount of C28 sterols is greater than C29 sterols. In some embodiments, the C28 sterol is ergosterol. In some embodiments, β-sitosterol, camperserol, stigmaserol, or cholesterol are not the most abundant sterols.

In some embodiments, the compositions provided herein comprise one or more of: ergosterol;
ergosterol and β-sitosterol, wherein the ratio of ergosterol to β-sitosterol is greater than 6:1; ergosterol and brassicasterol;

ergosterol, brassicasterol, and poriferasterol; and
wherein the composition is optionally free from one or more of β-sitosterol, campesterol, and stigmasterol.

In some embodiments, the compositions provided herein comprise a terpene. In some embodiments, the terpene is limonene.

In some embodiments, the compositions provided herein comprise a C1-C4 ester of lactic acid. In some embodiments, the lactic acid is ethyl lactate.

In some embodiments, the compositions provided herein comprise a surfactant. In some embodiments, the surfactant is a non-ionic surfactant.

In some embodiments, the compositions provided herein comprise an emulsifier.

In some embodiments, the compositions provided herein comprise water.

In some embodiments, provided is a microalgal cell comprising an exogenous nucleic acid having at least a 85% sequence identity to SEQ ID NO: 1. In some embodiments, the exogenous nucleic acid has at least a 90% sequence identity to SEQ ID NO: 1. In other embodiments, the exogenous nucleic acid has at least a 99% sequence identity to SEQ ID NO: 1.

In some embodiments, the microalgae is *Parachlorella, Chlorella,* or *Prototheca*. In some embodiments, the microalgae is *Prototheca*. In some embodiments, the microalgae is *Prototheca moriformis*.

In some embodiments, provided is a method for preparing a composition comprising C1-C4 esters of fatty acids derived from oil produced by a microalgae, the composition having a reduced odor compared to a composition where all the fatty acids are derived from vegetable oil, the method comprising:
a) providing oil produced by a microalgae, the oil comprising triacylglycerides having a fatty acid profile wherein the most abundant fatty acids are C12:0 fatty acids; and
b) treating the triacylglycerides with a C1-C4 alcohol under transesterification conditions to form C1-C4 esters of the microalgal derived fatty acids.

In some embodiments, provided is a method for preparing a composition comprising C1-C4 esters of fatty acids derived from oil produced by a microalgae, the composition having a reduced odor compared to a composition where all the fatty acids are derived from vegetable oil, the method comprising:
a) culturing a microalgal cell comprising an exogenous nucleic acid sequence to produce an oil comprising triacylglycerides having a fatty acid profile wherein the most abundant fatty acids are C12:0 fatty acids; and
b) treating the oil with a C1-C4 alcohol under transesterification conditions to form C1-C4 esters of microalgal derived fatty acids.

In some embodiments, the C1-C4 alcohol is methanol, ethanol, propanol, iso-propanol, butanol, or a tert-butanol. In some embodiments, the C1-C4 alcohol is methanol. In some embodiments, the C1-C4 alcohol is ethanol. In some embodiments, the C1-C4 alcohol is iso-propanol.

In some embodiments, the transesterification conditions comprise an acid or base catalyst. In some embodiments, the base catalyst is KOH.

In some embodiments, the method provided herein further comprise blending the C1-C4 esters of fatty acids with one or more of a terpene, a C1-C4 ester of lactic acid, a surfactant, an emulsifier, or water. In some embodiments, the terpene is limonene. In some embodiments, the C1-C4 ester of lactic acid is ethyl lactate.

In some embodiments, the composition is a cleaner, a corrosion inhibitor, a lubricant, a metal working fluid, an ink carrier, a mold release agent, a polystyrene recycling solvent, a drilling fluid, a drilling loss control agent, a completion fluid, a work-over fluid, or a combination thereof.

In some embodiments, the cleaner is an adhesive remover, a driveway cleaner, a degreaser, a graffiti remover, hand cleaner, a waterless hand cleaner, a paint brush cleaner, a paint stripper, a varnish remover, a rubber tire remover, a wipe, a bug remover, a tar remover, a car wash cleaner, a parts cleaner, an engine cleaner, a fuel system additive, a rig wash, a heavy residue cleaner, a down-hole cleaner, a concrete down-hole cleaner, an ink roller cleaner, or a screen printing ink wash or a combination thereof. In some embodiments, provided are cleaners for paints, inks, coatings, sealants, elastomers, and polymers.

In some embodiments, the lubricant is a hydraulic fluid, a gear lube, a bearing lube, crankcase lube, a cylinder lube, a compressor lube, a turbine lube, a chain lube, a conveyor lube, a total-loss lube, wire rope lube, a cutting lube, stamping lube, a metal forming lube, a food grade lube, a grease, or a 2-stroke engine lube or a combination thereof.

In some embodiments, the metal working fluid is a metal forming, metal cutting, or a metal finishing fluid or a combination thereof.

In some embodiments, provided is a paint or ink.

In some embodiment provided is an oil & gas down-hole fluids or mud comprising an alkyl ester provided herein.

In some embodiments, the drilling fluid is a water based drilling fluid.

In some embodiments, provided is a method for treating a wellbore, comprising administering the composition provided herein. In some embodiments, the composition removes unwanted deposits. In some embodiments the unwanted deposit is crude oil. In some embodimetns, the unwanted deposit is asphaltenes, hydrogen sulfide, paraffins, scales, fines sulfur, heavy oil by-products, water blocks, drilling fluids, cement filtrates, kill fluids, pipe, dope, hydrocarbon emulsions, oil based muds, or water based muds.

In some embodiments, the wellbore is a vertical, horizontal, or deviated wellbore. In some embodiments, the wellbore is a vertical or horizontal wellbore. In other embodiments, the wellbore comprises a cement casing. In some embodiments the compositions provided herein are for use before or after cementing of a wellbore.

DETAILED DESCRIPTION

I. Definitions

"Biomass" is material produced by growth and/or propagation of cells. Biomass may contain cells and/or intracellular contents as well as extracellular material, includes, but is not limited to, compounds secreted by a cell. Biomass isolated from fermentation broth may include nutrients and feedstock used to grow the cells.

"Exogenous gene" shall mean a nucleic acid that codes for the expression of an RNA and/or protein that has been introduced into a cell (e.g. by transformation/transfection), and is also referred to as a "transgene". A cell comprising an exogenous gene may be referred to as a recombinant cell, into which additional exogenous gene(s) may be introduced. The exogenous gene may be from a different species (and so heterologous), or from the same species (and so homologous), relative to the cell being transformed. Thus, an exogenous gene can include a homologous gene that occupies a different location in the genome of the cell or is under different control, relative to the endogenous copy of the gene. An exogenous gene may be present in more than one copy in the cell. An exogenous gene may be maintained in a cell as an insertion into the genome (nuclear or plastid) or as an episomal molecule.

"Fatty acids" shall mean free fatty acids, fatty acid salts, or fatty acyl moieties in a glycerolipid. It will be understood that fatty acyl groups of glycerolipids can be described in terms of the carboxylic acid or anion of a carboxylic acid that is produced when the triglyceride is hydrolyzed or saponified.

"Fixed carbon source" is a molecule(s) containing carbon, typically an organic molecule that is present at ambient temperature and pressure in solid or liquid form in a culture media that can be utilized by a microorganism cultured therein. Accordingly, carbon dioxide is not a fixed carbon source.

"In operable linkage" is a functional linkage between two nucleic acid sequences, such a control sequence (typically a promoter) and the linked sequence (typically a sequence that encodes a protein, also called a coding sequence). A promoter is in operable linkage with an exogenous gene if it can mediate transcription of the gene.

"Microalgae" are eukaryotic microbial organisms that contain a chloroplast or other plastid, and optionally that is capable of performing photosynthesis, or a prokaryotic microbial organism capable of performing photosynthesis. Microalgae include obligate photoautotrophs, which cannot metabolize a fixed carbon source as energy, as well as heterotrophs, which can live solely off of a fixed carbon source. Microalgae include unicellular organisms that separate from sister cells shortly after cell division, such as *Chlamydomonas*, as well as microbes such as, for example, *Volvox*, which is a simple multicellular photosynthetic microbe of two distinct cell types. Microalgae include cells such as *Chlorella, Dunaliella,* and *Prototheca*. Microalgae also include other microbial photosynthetic organisms that exhibit cell-cell adhesion, such as *Agmenellum, Anabaena,* and *Pyrobotrys*. Microalgae also include obligate heterotrophic microorganisms that have lost the ability to perform photosynthesis, such as certain dinoflagellate algae species and species of the genus *Prototheca*.

An "oleaginous" cell is a cell capable of producing at least 20% lipid by dry cell weight, naturally or through recombinant or classical strain improvement. An "oleaginous microbe" or "oleaginous microorganism" is a microbe, including a microalga that is oleaginous. An oleaginous cell also encompasses a cell that has had some or all of its lipid or other content removed, and both live and dead cells.

A "natural oil" or "natural fat" shall mean a predominantly triglyceride oil obtained from an organism, where the oil has not undergone blending with another natural or synthetic oil, or fractionation so as to substantially alter the fatty acid profile of the triglyceride. In connection with an oil comprising triglycerides of a particular regiospecificity, the natural oil or natural fat has not been subjected to interesterification or other synthetic process to obtain that regiospecific triglyceride profile, rather the regiospecificity is produced naturally, by a cell or population of cells. In connection with a natural oil or natural fat, and as used generally throughout the present disclosure, the terms oil and fat are used interchangeably, except where otherwise noted. Thus, an "oil" or a "fat" can be liquid, solid, or partially solid at room temperature, depending on the makeup of the substance and other conditions. Here, the term "fractionation" means removing material from the oil in a way that changes its fatty acid profile relative to the profile produced by the organism, however accomplished. The terms "natural oil" and "natural fat" encompass such oils obtained from an organism, where the oil has undergone minimal processing, including refining, bleaching and/or degumming, that does not substantially change its triglyceride profile. A natural oil can also be a "noninteresterified natural oil", which means that the natural oil has not undergone a process in which fatty acids have been redistributed in their acyl linkages to glycerol and remain essentially in the same configuration as when recovered from the organism.

In connection with a natural oil, a "profile" is the distribution of particular species or triglycerides or fatty acyl groups within the oil. A "fatty acid profile" is the distribution of fatty acyl groups in the triglycerides of the oil without reference to attachment to a glycerol backbone. Fatty acid profiles are typically determined by conversion to a fatty acid methyl ester (FAME), followed by gas chromatography (GC) analysis with flame ionization detection (FID). The fatty acid profile can be expressed as one or more percent of a fatty acid in the total fatty acid signal determined from the area under the curve for that fatty acid. FAME-GC-FID measurement approximate weight percentages of the fatty acids. A "sn-2 profile" is the distribution of fatty acids found at the sn-2 position of the triacylglycerides in the oil. A "regiospecific profile" is the distribution of triglycerides with reference to the positioning of acyl group attachment to the glycerol backbone without reference to stereospecificity. In other words, a regiospecific profile describes acyl group attachment at sn-$\frac{1}{3}$ vs. sn-2. Thus, in a regiospecific profile, POS (palmitate-oleate-stearate) and SOP (stearate-oleate-palmitate) are treated identically. A "stereospecific profile" describes the attachment of acyl groups at sn-1, sn-2 and sn-3. Unless otherwise indicated, triglycerides such as SOP and POS are to be considered equivalent. A "TAG profile" is the distribution of fatty acids found in the triglycerides with reference to connection to the glycerol backbone, but without reference to the regiospecific nature of the connections. Thus, in a TAG profile, the percent of SSO in the oil is the sum of SSO and SOS, while in a regiospecific profile, the percent of SSO is calculated without inclusion of SOS species in the oil. In contrast to the weight percentages of the FAME-GC-FID analysis, triglyceride percentages are typically given as mole percentages; that is the percent of a given TAG molecule in a TAG mixture.

The term "percent sequence identity," in the context of two or more amino acid or nucleic acid sequences, refers to two or more sequences or subsequences that are the same or have a specified percentage of amino acid residues or nucleotides that are the same, when compared and aligned for maximum correspondence, as measured using a sequence comparison algorithm or by visual inspection. For sequence comparison to determine percent nucleotide or amino acid identity, typically one sequence acts as a reference sequence, to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters. Optimal alignment of sequences for comparison can be conducted using the NCBI BLAST software (ncbi.nlm.nih.gov/BLAST/) set to default parameters. For example, to compare two nucleic acid sequences, one may use blastn with the "BLAST 2 Sequences" tool Version 2.0.12 (Apr. 21, 2000) set at the following default parameters: Matrix: BLOSUM62; Reward for match: 1; Penalty for mismatch: −2; Open Gap: 5 and Extension Gap: 2 penalties; Gap×drop-off: 50; Expect: 10; Word Size: 11; Filter: on. For a pairwise comparison of two amino acid sequences, one may use the "BLAST 2 Sequences" tool Version 2.0.12 (Apr. 21, 2000) with blastp set, for example, at the following default parameters: Matrix: BLOSUM62; Open Gap: 11 and Extension Gap: 1 penalties; Gap×drop-off 50; Expect: 10; Word Size: 3; Filter: on.

"Recombinant" is a cell, nucleic acid, protein or vector that has been modified due to the introduction of an exogenous nucleic acid or the alteration of a native nucleic acid. Thus, e.g., recombinant cells can express genes that are not found within the native (non-recombinant) form of the cell or express native genes differently than those genes are expressed by a non-recombinant cell. Recombinant cells can, without limitation, include recombinant nucleic acids that encode for a gene product or for suppression elements such as mutations, knockouts, antisense, interfering RNA (RNAi) or dsRNA that reduce the levels of active gene product in a cell. A "recombinant nucleic acid" is a nucleic acid originally formed in vitro, in general, by the manipulation of nucleic acid, e.g., using polymerases, ligases, exonucleases, and endonucleases, using chemical synthesis, or otherwise is in a form not normally found in nature. Recombinant nucleic acids may be produced, for example, to place two or more nucleic acids in operable linkage. Thus, an isolated nucleic acid or an expression vector formed in vitro by ligating DNA molecules that are not normally joined in nature, are both considered recombinant for the purposes of this invention. Once a recombinant nucleic acid is made and introduced into a host cell or organism, it may replicate using the in vivo cellular machinery of the host cell; however, such nucleic acids, once produced recombinantly, although subsequently replicated intracellularly, are still considered recombinant for purposes of this invention. Similarly, a "recombinant protein" is a protein made using recombinant techniques, i.e., through the expression of a recombinant nucleic acid.

The terms "triglyceride", "triacylglyceride" and "TAG" are used interchangeably as is known in the art.

"Cleaners" or "solvents" refers to substances and products used (a) to wash, de-grease, clean, disinfect, buff, polish, shine or protect (i) buildings and facilities (including, without limitation, homes, factories, offices, hotels, convention centers, hospitals and medical facilities, schools and educational facilities, shops, restaurants, places of business, government and military facilities, warehouses and storage facilities, public and private utilities, oil and gas production rigs, parks and recreation facilities), (ii) hard surfaces (including, without limitation, floors, walls, ceilings, doors, windows, counters, tables, chairs, kitchen and appliance surfaces, laboratory surfaces and toilets), (iii) human or animal skin, and (iv) automotive or other transportation interior or exterior surfaces; (b), as fuel system additives. These cleaners include those commonly characterized in the cleaning industry as Home, Industrial & Institutional Cleaners.

"Lubricants" refers to substances introduced to reduce friction between moving surfaces. Industrial applications for lubricants include but are not limited to hydraulic fluids, industrial lubricants (such as gear oils, bearing oils, crankcase oils, cylinder oils, compressor oils, turbine oils, chain & conveyor oils, "total loss" lubricants, wire rope lubricants, cutting fluids, stamping lubes, metal forming lubes, food grade lubricants, greases, and engine oils such as two-stroke engine oils "Metalworking fluids" refers to fluids used in working with metals to create individual parts, assemblies, or large-scale structures. The fluids can be used in metal forming (e.g. sizing, casting, forging, extruding, heading, stamping, drawing, bending, hardening, rolling, shearing, blanking, fine-blanking, coining), metal cutting (e.g. machining, turning, milling, drilling, grinding, sawing, threading, reaming, gun drilling, broaching, riveting, cooling, cleaning), and metal finishing (e.g. de-burring, grinding, brushing, buffing, polishing, vibratory finishing).

"Oil & Gas Down-Hole Fluids and Muds" refers to substances or formulations (both oil and water based) introduced down-hole before, during or after oil and gas exploration, drilling, cementing and completion, production, stimulation, enhanced oil recovery and clean-up and remediation.

II. General

Illustrative embodiments of the present invention feature oleaginous cells that produce altered fatty acid profiles and/or altered regiospecific distribution of fatty acids in glycerolipids, and products produced from the cells. Examples of oleaginous cells include microbial cells having a type II fatty acid biosynthetic pathway, including plastidic oleaginous cells such as those of oleaginous algae. Specific examples of cells include heterotrophic or obligate heterotrophic microalgae of the phylum Chlorophyta, the class Trebouxiophytae, the order Chlorellales, or the family Chlorellacae. Examples of oleaginous microalgae and methods of cultivation are also provided in Published PCT Patent Applications WO2008/151149, WO2010/06032, WO2011/150410, WO2011/150411, WO2012/061647, and WO2012/106560, including species of *Chlorella* and *Prototheca*, a genus comprising obligate heterotrophs. The oleaginous cells can be, for example, capable of producing 25, 30, 40, 50, 60, 70, 80, 85, or about 90% oil by cell weight, ±5%. Optionally, the oils produced can be low in highly unsaturated fatty acids such as DHA or EPA fatty acids. For example, the oils can comprise less than 5%, 2%, or 1% DHA and/or EPA. In some cases, the microalgal oils have a high oleic and low polyunsaturated fatty acid profile and derivatives of the oils, including acids, esters, epoxides, hydroxylated acids and esters, urethanes, amides, and polymers can be prepared with the same attributes for use in foodstuffs and in industrial and material applications. The above-mentioned publications also disclose methods for cultivating such cells and extracting oil, especially from microalgal cells; such methods are applicable to the cells disclosed herein and incorporated by reference for these teachings. When microalgal cells are used they can be cultivated autotrophically (unless an obligate heterotroph) or in the dark using a sugar (e.g., glucose, fructose and/or sucrose) In any of the embodiments described herein, the cells can be heterotrophic cells comprising an exogenous invertase gene so as to allow the cells to produce oil from a sucrose feedstock. Alternately, or in addition, the cells can metabolize xylose from cellulosic feedstocks. For example, the cells can be genetically engineered to express one or more xylose metabolism genes such as those encoding an active xylose transporter, a xylulose-5-phosphate transporter, a xylose isomerase, a xylulokinase, a xylitol dehydrogenase and a xylose reductase. See WO2012/154626, "GENETICALLY ENGINEERED MICROORGANISMS THAT METABOLIZE XYLOSE", published Nov. 15, 2012.

The oleaginous cells may, optionally, be cultivated in a bioreactor/fermenter. For example, heterotrophic oleaginous microalgal cells can be cultivated on a sugar-containing nutrient broth. Optionally, cultivation can proceed in two stages: a seed stage and a lipid-production stage. In the seed stage, the number of cells is increased from s starter culture. Thus, the seeds stage typically includes a nutrient rich, nitrogen replete, media designed to encourage rapid cell division. After the seeds stage, the cells may be fed sugar under nutrient-limiting (e.g. nitrogen sparse) conditions so that the sugar will be converted into triglycerides. For example, the rate of cell division in the lipid-production stage can be decreased by 50%, 80% or more relative to the seed stage. Additionally, variation in the media between the seed stage and the lipid-production stage can induce the recombinant cell to express different lipid-synthesis genes and thereby alter the triglycerides being produced. For example, as discussed below, nitrogen and/or pH sensitive promoters can be placed in front of endogenous or exogenous genes. This is especially useful when an oil is to be produced in the lipid-production phase that does not support optimal growth of the cells in the seed stage. In an example below, a cell has a fatty acid desaturase with a pH sensitive promoter so than an oil that is low in linoleic acid is produced in the lipid production stage while an oil that has adequate linoleic acid for cell division is produced during the seed stage. The resulting low linoleic oil has exceptional oxidative stability.

The oleaginous cells express one or more exogenous genes encoding fatty acid biosynthesis enzymes. As a result, some embodiments feature natural oils that were not obtainable from a non-plant or non-seed oil, or not obtainable at all.

The oleaginous cells produce a storage oil, which is primarily triacylglyceride and may be stored in storage bodies of the cell. A raw oil may be obtained from the cells by disrupting the cells and isolating the oil. The raw oil may comprise sterols produced by the cells. WO2008/151149, WO2010/06032, WO2011/150410, WO2011/1504 WO2012/061647, and WO2012/106560 disclose heterotrophic cultivation and oil isolation techniques. For example, oil may be obtained by providing or cultivating, drying and pressing the cells. The oils produced may be refined, bleached and deodorized (RBD) as known in the art or as described in WO2010/120939. The raw or RBD oils may be used in a variety of food, chemical, and industrial products or processes. Even after such processing, the oil may retain a sterol profile characteristic of the source. Microalgal sterol profiles are disclosed below.

In some embodiments the triglycerides can be isolated from oleaginous microbes by mechanical pressing with pressure sufficient to extract oil. In various embodiments, the pressing step will involve subjecting the oleaginous microbes to at least 10,000 psi of pressure. In various embodiments, the pressing step involves the application of pressure for a first period of time and then application of a higher pressure for a second period of time. This process may be repeated one or more times ("oscillating pressure"). In various embodiments, moisture content of the oleaginous microbes is controlled during the pressing step. In various embodiments, the moisture is controlled in a range of from 0.1% to 3% by weight.

Expeller presses (screw presses) are routinely used for mechanical extraction of oil from soybeans and oil seeds. Generally, the main sections of an expeller press include an intake, a rotating feeder screw, a cage or barrel, a worm shaft and an oil pan. The expeller press is a continuous cage press, in which pressure is developed by a continuously rotating worm shaft. An extremely high pressure, approximately 10,000-20,000 pounds per square inch, is built up in the cage or barrel through the action of the worm working against an adjustable choke, which constricts the discharge of the pressed cake (spent biomass) from the end of the barrel. In various embodiments, screw presses from the following manufacturers are suitable for use: Anderson International Corp. (Cleveland, Ohio), Alloco (Santa Fe, Argentina), De Smet Rosedowns (Humberside, UK), The Dupps Co. (Germantown, Ohio), Grupo Tecnal (Sao Paulo, Brazil), Insta Pro (Des Moines, Iowa), French Oil Mill (Piqua, Ohio), Harburg Freudenberger (previously Krupp Extraktionstechnik) (Hamburg, Germany), Maschinenfabrik Reinartz (Neuss, Germany), Shann Consulting (New South Wales, Australia) and SKET (Magdeburg, Germany).

Where a fatty acid profile of a triglyceride (also referred to as a "triacylglyceride" or "TAG") cell oil is given here, it will be understood that this refers to a nonfractionated sample of the storage oil extracted from the cell analyzed under conditions in which phospholipids have been removed or with an analysis method that is substantially insensitive to the fatty acids of the phospholipids (e.g. using chromatography and mass spectrometry). The oil may be subjected to an RBD process to remove phospholipids, free fatty acids and odors yet have only minor or negligible changes to the fatty acid profile of the triglycerides in the oil. Because the cells are oleaginous, in some cases the storage oil will constitute the bulk of all the TAGs in the cell.

III. Minor Oil Components

The oils produced according to the above methods in some cases are made using a microalgal host cell. As described above, the microalga can be, without limitation, fall in the classification of Chlorophyta, Trebouxiophyceae, Chlorellales, Chlorellaceae, or Chlorophyceae. It has been found that microalgae of Trebouxiophyceae can be distinguished from vegetable oils based on their sterol profiles. Oil produced by *Chlorella protothecoides* was found to produce sterols that appeared to be brassicasterol, ergosterol, campesterol, stigmasterol, and β-sitosterol, when detected by GC-MS. However, it is believed that all sterols produced by *Chlorella* have C24β stereochemistry. Thus, it is believed that the molecules detected as campesterol, stigmasterol, and β-sitosterol, are actually 22,23-dihydrobrassicasterol, poriferasterol and clionasterol, respectively. Thus, the oils produced by the microalgae described above can be distinguished from plant oils by the presence of sterols with C24β stereochemistry and the absence of C24α stereochemistry in the sterols present. For example, the oils produced may contain 22,23-dihydrobrassicasterol while lacking campesterol; contain clionasterol, while lacking in β-sitosterol, and/or contain poriferasterol while lacking stigmasterol. Alternately, or in addition, the oils may contain significant amounts of $\Delta^7$-poriferasterol.

In one embodiment, the oils provided herein are not vegetable oils. Vegetable oils are oils extracted from plants and plant seeds. Vegetable oils can be distinguished from the non-plant oils provided herein on the basis of their oil content. A variety of methods for analyzing the oil content can be employed to determine the source of the oil or whether adulteration of an oil provided herein with an oil of a different (e.g. plant) origin has occurred. The determination can be made on the basis of one or a combination of the analytical methods. These tests include but are not limited to analysis of one or more of free fatty acids, fatty acid profile, total triacylglycerol content, diacylglycerol content, peroxide values, spectroscopic properties (e.g. UV absorption), sterol profile, sterol degradation products, antioxidants (e.g. tocopherols), pigments (e.g. chlorophyll), d13C values and sensory analysis (e.g. taste, odor, and mouth feel). Many such tests have been standardized for commercial oils such as the Codex Alimentarius standards for edible fats and oils.

Sterol profile analysis is a particularly well-known method for determining the biological source of organic matter. Campesterol, β-sitosterol, and stigmasterol are common plant sterols, with β-sitosterol being a principle plant sterol. For example, β-sitosterol was found to be in greatest abundance in an analysis of certain seed oils, approximately 64% in corn, 29% in rapeseed, 64% in sunflower, 74% in cottonseed, 26% in soybean, and 79% in olive oil (Gul et al. J. Cell and Molecular Biology 5:71-79, 2006).

Oil isolated from *Prototheca moriformis* strain UTEX 1435 were separately clarified (CL), refined and bleached (RB), or refined, bleached and deodorized (RBD) and were tested for sterol content according to the procedure described in JAOCS vol. 60, no. 8, Aug. 1983. Results of the analysis are shown below (units in mg/100 g):

| Sterol | Crude | Clarified | Refined & bleached | Refined, bleached, & deodorized |
|---|---|---|---|---|
| Ergosterol | 384 (56%) | 398 (55%) | 293 (50%) | 302 (50%) |
| 5,22-cholestadien-24-methyl-3-ol (Brassicasterol) | 14.6 (2.1%) | 18.8 (2.6%) | 14 (2.4%) | 15.2 (2.5%) |
| 24-methylcholest-5-en-3-ol (Campesterol or 22,23-dihydrobrassicasterol) | 10.7 (1.6%) | 11.9 (1.6%) | 10.9 (1.8%) | 10.8 (1.8%) |
| 5,22-cholestadien-24-ethyl-3-ol (Stigmasterol or poriferasterol) | 57.7 (8.4%) | 59.2 (8.2%) | 46.8 (7.9%) | 49.9 (8.3%) |
| 24-ethylcholest-5-en-3-ol (β-Sitosterol or clionasterol) | 9.64 (1.4%) | 9.92 (1.4%) | 9.26 (1.6%) | 10.2 (1.7%) |
| Other sterols | 209 | 221 | 216 | 213 |
| Total sterols | 685.64 | 718.82 | 589.96 | 601.1 |

These results show three striking features. First, ergosterol was found to be the most abundant of all the sterols, accounting for about 50% or more of the total sterols. The amount of ergosterol is greater than that of campesterol, β-sitosterol, and stigamsterol combined. Ergosterol is steroid commonly found in fungus and not commonly found in plants, and its presence particularly in significant amounts serves as a useful marker for non-plant oils. Secondly, the oil was found to contain brassicasterol. With the exception of rapeseed oil, brassicasterol is not commonly found in plant based oils. Thirdly, less than 2% β-sitosterol was found to be present. β-sitosterol is a prominent plant sterol not commonly found in microalgae, and its presence particularly in significant amounts serves as a useful marker for oils of plant origin. In summary, *Prototheca moriformis* strain UTEX1435 has been found to contain both significant amounts of ergosterol and only trace amounts of β-sitosterol as a percentage of total sterol content. Accordingly, the ratio of ergosterol:β-sitosterol or in combination with the presence of brassicasterol can be used to distinguish this oil from plant oils.

In some embodiments, the oil content of an oil provided herein contains, as a percentage of total sterols, less than 20%, 15%, 10%, 5%, 4%, 3%, 2%, or 1% β-sitosterol. In other embodiments the oil is free from β-sitosterol.

In some embodiments, the oil is free from one or more of β-sitosterol, campesterol, or stigmasterol. In some embodiments the oil is free from β-sitosterol, campesterol, and stigmasterol. In some embodiments the oil is free from campesterol. In some embodiments the oil is free from stigmasterol.

In some embodiments, the oil content of an oil provided herein comprises, as a percentage of total sterols, less than 20%, 15%, 10%, 5%, 4%, 3%, 2%, or 1% 24-ethylcholest-5-en-3-ol. In some embodiments, the 24-ethylcholest-5-en-3-ol is clionasterol. In some embodiments, the oil content of an oil provided herein comprises, as a percentage of total sterols, at least 1%, 2%, 3%, 4%, 5%, 6%, 7%, 8%, 9%, or 10% clionasterol.

In some embodiments, the oil content of an oil provided herein contains, as a percentage of total sterols, less than 20%, 15%, 10%, 5%, 4%, 3%, 2%, or 1% 24-methylcholest-5-en-3-ol. In some embodiments, the 24-methylcholest-5-en-3-ol is 22,23-dihydrobrassicasterol. In some embodiments, the oil content of an oil provided herein comprises, as a percentage of total sterols, at least 1%, 2%, 3%, 4%, 5%, 6%, 7%, 8%, 9%, or 10% 22,23-dihydrobrassicasterol.

In some embodiments, the oil content of an oil provided herein contains, as a percentage of total sterols, less than 20%, 15%, 10%, 5%, 4%, 3%, 2%, or 1% 5,22-cholestadien-24-ethyl-3-ol. In some embodiments, the 5,22-cholestadien-24-ethyl-3-ol is poriferasterol. In some embodiments, the oil content of an oil provided herein comprises, as a percentage of total sterols, at least 1%, 2%, 3%, 4%, 5%, 6%, 7%, 8%, 9%, or 10% poriferasterol.

In some embodiments, the oil content of an oil provided herein contains ergosterol or brassicasterol or a combination of the two. In some embodiments, the oil content contains, as a percentage of total sterols, at least 5%, 10%, 20%, 25%, 35%, 40%, 45%, 50%, 55%, 60%, or 65% ergosterol. In some embodiments, the oil content contains, as a percentage of total sterols, at least 25% ergosterol. In some embodiments, the oil content contains, as a percentage of total sterols, at least 40% ergosterol. In some embodiments, the oil content contains, as a percentage of total sterols, at least 5%, 10%, 20%, 25%, 35%, 40%, 45%, 50%, 55%, 60%, or 65% of a combination of ergosterol and brassicasterol.

In some embodiments, the oil content contains, as a percentage of total sterols, at least 1%, 2%, 3%, 4% or 5% brassicasterol. In some embodiments, the oil content contains, as a percentage of total sterols less than 10%, 9%, 8%, 7%, 6%, or 5% brassicasterol.

In some embodiments the ratio of ergosterol to brassicasterol is at least 5:1, 10:1, 15:1, or 20:1.

In some embodiments, the oil content contains, as a percentage of total sterols, at least 5%, 10%, 20%, 25%, 35%, 40%, 45%, 50%, 55%, 60%, or 65% ergosterol and less than 20%, 15%, 10%, 5%, 4%, 3%, 2%, or 1% β-sitosterol. In some embodiments, the oil content contains, as a percentage of total sterols, at least 25% ergosterol and less than 5% β-sitosterol. In some embodiments, the oil content further comprises brassicasterol.

Sterols contain from 27 to 29 carbon atoms (C27 to C29) and are found in all eukaryotes. Animals exclusively make C27 sterols as they lack the ability to further modify the C27 sterols to produce C28 and C29 sterols. Plants however are able to synthesize C28 and C29 sterols, and C28/C29 plant sterols are often referred to as phytosterols. The sterol profile of a given plant is high in C29 sterols, and the primary sterols in plants are typically the C29 sterols β-sitosterol and stigmasterol. In contrast, the sterol profile of non-plant organisms contain greater percentages of C27 and C28 sterols. For example the sterols in fungi and in many microalgae are principally C28 sterols. The sterol profile and particularly the striking predominance of C29 sterols over C28 sterols in plants has been exploited for determining the proportion of plant and marine matter in soil samples (Huang, Wen-Yen, Meinschein W. G., "Sterols as ecological indicators"; Geochimica et Cosmochimia Acta. Vol 43. pp 739-745).

In some embodiments the primary sterols in the microalgal oils provided herein are sterols other than β-sitosterol and stigmasterol. In some embodiments of the microalgal oils, C29 sterols make up less than 50%, 40%, 30%, 20%, 10%, or 5% by weight of the total sterol content.

In some embodiments the microalgal oils provided herein contain C28 sterols in excess of C29 sterols. In some embodiments of the microalgal oils, C28 sterols make up greater than 50%, 60%, 70%, 80%, 90%, or 95% by weight of the total sterol content. In some embodiments the C28 sterol is ergosterol. In some embodiments the C28 sterol is brassicasterol.

IV. Drilling, Production, and Pumping-Services Fluids

The fluids provided herein include aqueous and non-aqueous drilling fluids and other well-related fluids including those used for production of oil or natural gas, for completion operations, sand control operations, workover operations, and for pumping-services such as cementing, hydraulic fracturing, and acidification. In one embodiment, a fluid includes a fluid loss control agent that is biomass from an oleaginous microbe. In one embodiment, the biomass comprises intact, lysed or partly lysed cells with greater than 5%, 10%, 20%, 30%, 40%, 50%, 60%, 70%, 80%, or 90% oil. In another embodiment, the biomass is spent biomass from which oil has been removed. For example, the oil may be removed by a process of drying and pressing and optionally solvent-extracting with hexane or other suitable solvent. In a specific embodiment, the biomass is dried to less than 6% moisture by weight, followed by application of pressure to release more than 25% of the lipid. Alternately, the cells may be intact, which, when used in a drilling fluid, may impart improved fluid-loss control in certain circumstances. Generally, the drilling fluid can contain about 0.1% to about 20% by weight of said biomass, but in various embodiments, this amount may range from about 0.1% to about 10% by weight of said biomass; from about 0.1% to about 5% by weight of said biomass; from about 0.5% to about 4% by weight of said biomass; and from about 1% to about 4% by weight of said biomass.

In various embodiments, the fluid comprises a fluid loss control agent that is not derived from oleaginous microbial biomass. Suitable fluid loss control agents may include, but are not limited to, unmodified starch, hydroxypropl starch, carboxymethyl starch, unmodified cellulose, carboxymethylcellulose, hydroxyethyl cellulose, and polyanionic cellulose.

The fluid can include an aqueous or non-aqueous solvent. The fluid can also optionally include one or more additional components so that the fluid is operable as a drilling fluid, a drill-in fluid, a workover fluid, a spotting fluid, a cementing fluid, a reservoir fluid, a production fluid, a fracturing fluid, or a completion fluid.

In various embodiments, the fluid is a drilling fluid and the added biomass from the oleaginous microbe serves to help transport cuttings, lubricate and protect the drill bit, support the walls of the well bore, deliver hydraulic energy to the formation beneath the bit, and/or to suspend cuttings in the annulus when drilling is stopped.

When used in a drilling fluid, the biomass may operate to occlude pores in the formation, and to form or promote the formation of a filter cake.

In various embodiments, the fluid is a production fluid and the biomass serves to inhibit corrosion, separate hydrocarbons from water, inhibit the formation of scale, paraffin, or corrosion (e.g., metal oxides), or to enhance production of oil or natural gas from the well. In an embodiment, the biomass is used to stimulate methanogenesis of microbes in the well. The biomass may provide nutrients and/or bind inhibitors so as to increase production of natural gas in the well. In this embodiment, the well can be a coal seam having methane generating capacity. See, for example, US Patent Application Nos. 2004/0033557, 2012/0021495, 2011/0284215, US2010/0248322, 2010/0248321, 2010/0035309, and 2007/0248531.

In various embodiments, the fluid comprises a viscosifier. Suitable viscosifiers include, but are not limited to, an alginate polymer selected from the group consisting of sodium alginate, sodium calcium alginate, ammonium calcium alginate, ammonium alginate, potassium alginate, propyleneglycol alginate, and mixtures thereof. Other suitable viscosifiers include organophillic clay, polyacrylamide, xanthan gum, and mixtures of xanthan gum and a cellulose derivative, including those wherein the weight ratio of xanthan gum to cellulose derivative is in the range from about 80:20 to about 20:80, and wherein the cellulose derivative is selected from the group consisting of hydroxyethylcellulose, hydroxypropylcellulose, carboxymethylcellulose and mixtures thereof. Other suitable viscosifiers include a biopolymer produced by the action of bacteria, fungi, or other microorganisms on a suitable substrate.

Mixtures of a bentonitic clay and additives can also be used as viscosifiers. The additives used in such mixtures can comprise, for example: (a) a nonionic, water-soluble polysaccharide selected from the group consisting of a non-ionic, water-soluble cellulosic derivative and a non-ionic water-soluble guar derivative; (b) an anionic water-soluble polysaccharide selected from the group consisting of a carboxymethyl cellulose and *Xanthomonas campestris* polysaccharide or a combination thereof; (c) an intermediate molecular weight polyglycol, i.e., selected from the group consisting of polyethylene glycol, polypropylene glycol, and poly-(alkanediol), having an average molecular weight of from about 600 to about 30,000; and (5) compatible mixtures thereof. Components of the mixtures may be added individually to the fluid to enhance the low shear rate viscosity thereof.

In some embodiments, the drilling fluid comprises one or more additives selected from the group consisting of an aphron, polymer particle, a thermoset polymer particle, and a nanocomposite particulate.

Aphrons can be used as additives to drilling fluids and other fluids used in creating or maintaining a borehole. Aphrons can concentrate at the fluid front and act as a fluid loss control agent and/or bridging agent to build an internal seal of the pore network along the sidewalls of a borehole. It is believed that aphrons deform during the process of sealing the pores and gaps encountered while drilling a borehole. Aphrons useful in the present methods are typically 50-100 µM, 25-100 µM, 25-50 µM, 5-50, 5-25 µM, 7-15 µM or about 10 µM.

In one embodiment, a drilling fluid comprises aphrons, microbial biomass in which the oil has not been extracted (unextracted microbial biomass), spent biomass or a combination of aphrons, unextracted microbial biomass, and spent biomass.

Where an aphron is used, the aphron can have an average diameter of 5 to 50 micrometers and can make up about 0.001% to 5% by mass of the fluid.

The use of drilling fluids containing polymer particle additives has several applications in construction, drilling, completion, and fracture simulation of oil and natural gas wells. These particles are generally spherical in shape, solid, and have a specific gravity of 1.06. The use of these particles provides several advantages, such as increasing mechanical lubrication, reducing equipment wear, and aiding in directional changes during sliding. These particles are generally resistant to deformation loads of up to >25,000 psi hydrostatic, and they display excellent resistance and thermal stability even at temperatures greater than 450° F. in a drilling environment. These particles can also be manufactured in fine or coarse grades, depending on the requirements of a particular drilling operation.

Polymer particles are easily added to drilling fluid through a mud-mixing hopper machine. When used to control torque and drag, these beads can be applied at concentrations of 2-8 ppb (5.71-22.87 kilograms/m$^3$). For spotting in wire-line operations and running casing, the polymer beads may be added to concentrations of 8-12 ppb (22.87-34.31 kilograms/m$^3$).

In some embodiments, the drilling fluid comprises a thermoset polymer particle such as those disclosed in U.S. Pat. No. 8,088,718. In some embodiments, the drilling fluid comprises a nanocomposite particulate such as those disclosed in US 2005/0272611. In some embodiments, the drilling fluid comprises a co-polymer bead such as Alpine Drill Beads commercially available from Alpine Specialty Chemicals (Houston, Tex.).

Examples of other additives that may be used in drilling applications include, but are not limited to: alkalinity agents, corrosion inhibitors, defoamers, dispersants, emulsifiers, fluid loss control agents, foaming agent for gas-based fluids, intermediates for corrosion inhibitor, lubricants, misting agents, oxygen scavengers, hydrosulfite scavengers, biocides, scale inhibitors, scale removers, shale inhibitors, solvents, specialty surfactants, thermal stabilizers, viscosifiers, and water purifiers.

The additives disclosed herein, e.g., including the polymeric and glass bead additives, can contribute to bursting and releasing oil from the microbial cells. In such instances the additives work in concert with the cells to provide delay-released lubrication to the drill bit. Though not intended to be limited by the following mechanism, in one aspect this application is directed to a pressure sensitive lubricant that allows for time-delayed release of a lubricating oil by virtue of the oil being encapsulated within a cell. In instances when the lubricant is used in a drilling fluid, the pressure that triggers the oil to be released is provided by the drill string and/or drill bit. The oil is released only when sufficient downhole pressure and/or friction is present. Such pressure and friction is provided by the drill string and/or drill bit in its interaction with the well formation, such as when it is dragged along the well-bore (particularly in the non-vertical portions of the well-bore) or during the rotational motion of the drill string/drill bit during drilling.

Additives and lubricants to be used in combination with the oleaginous cells and oils provided herein include commercially available lubricants. These lubricants can be blended with oleaginous cells and oils produced by these cells. The commercially available lubricants include those marketed by Baker Hughes (RHEO-LOGIC, MAGMA-TEQ, CARBO-DRIL, MPRESS, PERFORMAX, PERFLEX, TERRA-MAX, PYRO-DRILL, MAX-BRIDGE, CHEK-LOSS, LC-LUBE, MIL-CARB, SOLUFLAKE, FLOW-CARB, X-LINK crosslinked composition, and SOLU-SQUEEZE LCM), Haliburton (BAROID, BOREMAX, PERFOR-MADRIL, SHALEDRIL, SUPER-SAT, and BaraECD) and Schlumberger (DRILPLEX, DURATHERM, ENVIRO-THERM NT, GLYDRIL, K-MAG, KLA-SHIELD, SAGDRIL, ULTRADRIL, ECOGREEN, MEGADRIL, NOVAPLUS, PARADRIL, PARALAND, PARATHERM, RHADIANT, VERSACLEAN, VERSADRIL, and WARP fluids).

In various embodiments, the fluid comprises a density modifier, also known as a weighting agent or a weighting additive. Suitable density modifiers include, but are not limited to, barite, hematite, manganese oxide, calcium carbonate, iron carbonate, iron oxide, lead sulfide, siderate, and ilmenite.

In various embodiments, the fluid comprises an emulsifier. Suitable emulsifiers may be nonionic, including ethoxylated alkylphenols and ethoxylated linear alcohols, or anionic, including alkylaryl sulfonates, alcohol ether sulfonates, alkyl amine sulfonates, petroleum sulfonates, and phosphate esters.

In various embodiments, the fluid comprises a lubricant. Non-limiting, suitable lubricants may include fatty acids, tall oil, sulphonated detergents, phosphate esters, alkanolamides, asphalt sulfonates, graphite, and glass beads.

The fluid can be a drilling fluid with a low shear rate viscosity as measured with a Brookfield viscometer at 0.5 rpm of at least 20,000 centipoise. In some embodiments, the low shear rate viscosity is at least about 40,000 centipoise.

Biomass added to fluid can be chemically modified prior to use. Chemical modification involves the formation or breaking of covalent bonds. For example, the biomass may be chemically modified by transesterification, saponification, crosslinking or hydrolysis. The biomass may be treated with one or more reactive species so as to attach desired moieties. The moieties may be hydrophobic, hydrophilic, amphiphilic, ionic, or zwitterionic. For example, the biomass may anionized (e.g., carboxymethylated), or acetylated. Methods for covalent modification including carboxymethylation and acetylation of biomass from oleaginous microbes are disclosed in U.S. Provisional Patent Application No. 61/615,832, filed on Mar. 26, 2012 for "Algal Plastics and Absorbants", incorporated herein by reference in relevant part.

V. Alkyl Ester Preparation

Methods for producing alkyl esters are well known such as those described in U.S. Pat. No. 2,383,602 and U.S. Pat. No. 7,652,156. Triglycerides are contacted with excess alcohol in the presence of an acid, or more typically, a base catalyst. Suitable base catalysts include sodium hydroxide, lithium hydroxide, and potassium hydroxide. Upon completion of the transesterification reaction the heavier glycerol by-product separates from the alkyl ester as the lower of two layers and can be readily removed.

VI. Examples

Example 1

Strain A was derived from UTEX 1435 classically mutagenized for higher oil production and further transformed with plasmid pSZ1413 (SEQ ID NO:1) to disrupt a stearoyl-ACP desaturase site followed by further mutagenesis. The plasmid was constructed and transformed into *Prototheca* cells that were subsequently grown heterotrophically and pressed to extract oil in accordance with methods described in WO2008/151149, WO2010/063031, WO2010/063032, WO2011/150411, and WO2013/158938. The plasmid comprises a *C. reinhardtii* β-tubulin promoter driving the expression of a *Saccharomyces cerevisiae* sucrose invertase gene with a *Chlorella protothecoides* Ef1 3' UTR and a *Prototheca moriformis* endogenous AMTS promoter driving expression of an exogenous acyl-ACP thioesterase from *Cuphea. Wrightii* fused to a transit peptide from *Prototheca moriformis* fatty acid desaturase with a *Chlorella vulgaris* nitrate reductase 3' UTR. The extracted triglyceride oil was refined, bleached, and deodorized and found to have the fatty acid profile in Table 1 and the sterol content in Table 2. The fatty acid profile of strain A contain significant amounts of C12:0 fatty acids (50.72%), followed by C10:0 (19.35%) and C14:0 (13.28%) fatty acids. A comparison of the oil to coconut, palm kernel oil, and babassu oil (data from Codex Standard for Named Vegetable Oils) is also given in Table 1.

TABLE 1

FATTY ACID PROFILE (WEIGHT PERCENT) OF STRAIN A OIL IN COMPARISON TO COCONUT AND PALM KERNEL OIL.

| Fatty acid | Strain A | Coconut Oil | Palm Kernel Oil | Babassu Oil |
|---|---|---|---|---|
| C6:0 | | ND-0.7 | ND-0.8 | ND |
| C8:0 | 0.28 | 4.6-10.0 | 2.4-6.2 | 2.6-7.3 |
| C10:0 | 19.35 | 5.0-8.0 | 2.6-5.0 | 1.2-7.6 |
| C11:0 | 0.07 | | | |
| C12:0 | 50.72 | 45.1-53.2 | 45.0-55.0 | 40.0-55.0 |
| C12:1 | 0.05 | | | |
| C13:0 | 0.05 | | | |
| C14:0 | 13.28 | 16.8-21.0 | 14.0-18.0 | 11.0-27.0 |
| C14:1 cis-$\Delta^9$ | 0.02 | | | |
| C15:0 | 0.03 | | | |
| C16:0 | 5.24 | 7.5-10.2 | 6.5-10.0 | 5.2-11.0 |
| C16:1 cis-$\Delta^7$ | 0.02 | ND | ND-0.2 | ND |
| C16:1 cis-$\Delta^9$ | 0.11 | ND | ND | ND |
| C17:0 | 0.01 | ND | ND | ND |
| C18:0 | 0.35 | 2.0-4.0 | 1.0-3.0 | 1.8-7.4 |
| C18:1 | 6.78 | 5.0-10.0 | 12.0-19.0 | 9.0-20.0 |
| C18:2 | 2.47 | 1.0-2.5 | 1.0-3.5 | 1.4-6.6 |
| C18:2 trans, trans-$\Delta^9$, $\Delta^{12}$ | 0.01 | | | |
| C18:3 alpha (cis, cis, cis-$\Delta^9$, $\Delta^{12}$, $\Delta^{15}$) | 0.5 | ND-0.2 | ND-0.2 | ND |
| C20:0 | 0.03 | ND-0.2 | ND-0.2 | ND |
| C20:1 | 0.01 | ND-0.2 | ND-0.2 | ND |
| C20:1-1 | 0.03 | | | |
| C24:0 | 0.01 | ND | ND | ND |

ND = nondetectable, defined as ≤0.05%

TABLE 2

STEROL CONTENT OF STRAIN A OIL.

| Sterol | mg/100 g |
|---|---|
| Ergosterol | 154 |
| Campesterol | 4.92 |
| Stigmasterol | 6.26 |
| β-Sitosterol | 23.9 |
| Other sterols | 56.1 |

Example 2

Microalgal Derived Alkyl Esters

The triglyceride oil from Example 1 was transesterified with methanol and ethanol according to known transesterification methods. The methyl and ethyl esters were analyzed according to the methods in Table 3 below.

TABLE 3

PROPERTIES OF ALGAL DERIVED METHYL AND ETHYL ESTERS.

| Property | Method | Units | Methyl ester | Ethyl ester |
|---|---|---|---|---|
| Kauri-butanol value | ASTM D1133 | unit | 75-77.5 | 67 |
| Flash Point Pensky-Martens Closed Cup | ASTM D93a | ° C. | 113-120 | 116 |
| Kinematic Viscosity at 40° C. | ASTM D445 | mm$\hat{\,}$2/s | 2.7 | 3.2 |
| Residue on Evaporation | ASTM D1353 | mg/kg | 62 | 54 |
| Volatile Matter Content | EPA Method 24 | g/g | 0.93 | |
| VOC Content | EPA 24/ ASTM D2369 | Wt % | 0.513 g/g | |
| Vapor Pressure (DVPE) | ASTM D5191 | psi | | 0.63 |
| Gardner Color | ASTM D1544 | unit | 3 | |
| Methanol | EN14110 | mass % | 0.01 | |
| Water and Sediment | ASTM D2709 | volume % | 0 | 0.0 |
| Free Glycerin | ASTM D6584 | mass % | 0.001 | 0.012 |
| Total Glycerin | ASTM D6584 | mass % | 0.034 | 0.143 |
| Monoglycerides | ASTM D6584 | mass % | 0.09 | |
| Diglycerides | ASTM D6584 | mass % | 0.054 | |
| Triglycerides | ASTM D6584 | mass % | 0.02 | |
| Ester Content | Internal Method | mass % | 99.8 | |
| Vapor Pressure @ 20 C. | ASTM D5191 | mmHg | <1 psi | <1 psi |

Example 3

Solvent Compositions

Solvents formulations with or without the methyl ester of Example 2 (Solvent M) were prepared according to Table 4.

TABLE 4

SOLVENT FORMULATIONS.

| Component | d-limonene solvent | C10 Solvent | Solvent M | Xylene solvent |
|---|---|---|---|---|
| d-limonene (technical grade) | 20 | 0 | 0 | 0 |
| CE-1095 (P&G Cehmicals) | 0 | 20 | 0 | 0 |
| Example 2, Methyl Ester | 0 | 0 | 20 | 0 |
| Xylene (ACS reagent grade) | 0 | 0 | 0 | 20 |
| Videt ME-80 | 13.5 | 20.72 | 20.72 | 15.5 |
| Rexonic N91-8 | 3 | 3 | 3 | 3 |
| Water (deionized) | 63.5 | 56.28 | 56.28 | 61.5 |

Example 4

Cleaning Performance Testing

The formulations in Example 3 were tested for cleaning performance in the removal of bitumen, crude oil, and drilling mud.
Equipment Used: Gardner Blue Straight-Line Washability Machine
    Nikon Camera
    Gardco Adjustable Micrometer Microm II Film Applicator, (ASTM D823)
    Image Analysis Software
    10.00 mL pipette
    Grieve Forced Air oven
    ASTM D4488 A5, brass template
Materials: Bitumen, LC#: 13-T0551
    Used Drilling Mud, LC#: 10-T1155
    Crude Oil, LC#: 13-T1134
    3M Cellulose Sponge 304 brushed Stainless Steel panels, 15.0 cm×10.0 cm
Bitumen Soil Application:
Soil Application for Testing of 20% Active Solvent Emulsions Applied Bitumen to 304 brushed SS panels using A5 brass template and thinning out to an even film via a kim wipe (length of template was along shorter edge of panel (10 cm edge), application weight was 0.35 grams. Panels sit over night at ambient conditions for a minimum of 18 hours before testing.
Soil Application for Testing of 100% Solvent Applied the bitumen to 304 brushed SS panels, 154569, using the Gardco Adjustable Film applicator. The applicator was set to a gap of 0.500 mm. The panels were put into the forced air oven set to 800 C, (preheated). The panels were put into the oven for 24.0 hours. Cooled under ambient conditions for two hours prior to testing.
Used Drilling Mud Soil Application:
Soil Application for Testing of 20% Active Solvent Emulsions Applied used drilling mud to 304 brushed SS panels and thinning out to an even film using the Gardco Adjustable Film applicator. The applicator was set to a gap of 0.300 mm. The panels were put into the forced air oven set to 800 C, (preheated) for 20 hours. Panels were removed at exactly 20 hours after putting into the preheated oven. The oven was preheated to 2000 C and the panels were put into the oven for 120 minutes. Cooled under ambient conditions for two hours prior to testing.
Soil Application for Testing of 100% Solvent Applied used drilling mud to 304 brushed SS panels and thinning out to an even film using the Gardco Adjustable Film applicator. The applicator was set to a gap of 0.300 mm. The panels were put into the forced air oven set to 80° C., (preheated) for 20 hours. Panels were removed at exactly 20 hours after putting into the preheated oven. The oven was preheated to 200° C. and the panels were put into the oven for 70 minutes. Cooled under ambient conditions for two hours prior to testing.
Crude Oil Soil Application
Soil Application for Testing of 20% Active Solvent Emulsions Applied crude oil to 304 brushed SS panels and thinning out to an even film using the Gardco Adjustable Film applicator. The applicator was set to a gap of 0.300 mm. The panels were put into the forced air oven set to 1000 C, (preheated). Panels were removed at exactly 20 hours after putting into the preheated oven. Cooled under ambient conditions for two hours prior to testing
Soil Application for Testing of 100% Solvent Applied crude oil to 304 brushed SS panels and thinning out to an even film using the Gardco Adjustable Film applicator. The applicator was set to a gap of 0.300 mm. The panels were put into the forced air oven set to 800 C, (preheated) for 20 hours. Panels were removed at exactly 20 hours after putting into the preheated oven. The oven was preheated to 2000 C and the panels were put into the oven for 120 minutes. Cooled under ambient conditions for two hours prior to testing.
Cleaning Test Condition the small cellulose sponge as per ASTM D4488 A5 Method.

The organic solvent product is tested at a 20% by weight concentration as per the specified base formulation or as supplied, (100% active solvent). The soiled and aged panel is placed on the Gardner Straight-line washability apparatus using a template. Apply 10.00 mL of the solvent to the pre-conditioned sponge and invert the sponge onto the soil. Start the Gardner machine and run the machine until approximately 70-90% of the soil has been removed by the test solvent. After the machine is stopped, rinse with a cool stream of tap water. Air-dry the panels before evaluation.
Evaluation Using the Nikon camera and lighting booth, take a digital picture of the cleaned panel. Analyse the image using the image analysis software to quantify the percentage of grease removed from the surface. Report the average percentage removed and the average number of cycles required to achieve the percentage removed.

The results of the cleaning performance of the solvents are given in Tables 5-7 below.

TABLE 5

CLEANING EFFICIENCY OF BITUMEN GREASE REMOVAL.

| Organic Solvent | Average # Cycles | Average % Removal |
| --- | --- | --- |
| 20% Xylene emulsion | 30 | 88.5 |
| 20% d-Limonene emulsion | 80 | 86.5 |
| 20% CE-1095 emulsion | 95 | 84 |
| 20% Solvent M | 115 | 76.2 |
| 100% xylene | 37 | 94.7 |
| 100% d-Limonene | 70 | 83.5 |
| 100% CE-1095 | 73 | 86.7 |
| 100% Solvent M | 143 | 78.7 |

TABLE 6

CLEANING EFFICIENCY OF USED DRILLING MUD REMOVAL.

| Organic Solvent | Average # Cycles | Average % Removal |
| --- | --- | --- |
| 20% Xylene emulsion | 15 | 80.2 |
| 20% d-Limonene emulsion | 19 | 84.1 |
| 20% CE-1095 emulsion | 33 | 80.5 |
| 20% Solvent M | 33 | 78.1 |
| 100% xylene | 33 | 62.3 |
| 100% d-Limonene | 48 | 64.6 |
| 100% CE-1095 | 48 | 73.8 |
| 100% Solvent M | 47 | 77.6 |

TABLE 7

CLEANING EFFICIENCY CRUDE OIL REMOVAL.

| Organic Solvent | Average # Cycles | Average % Removal |
| --- | --- | --- |
| 20% Xylene emulsion | 30 | 73.7 |
| 20% d-Limonene emulsion | 63 | 82.7 |
| 20% CE-1095 emulsion | 177 | 77.7 |
| 20% Solvent M | 200 | 84.8 |
| 100% xylene | 3 | 93.4 |
| 100% d-Limonene | 2 | 92.9 |
| 100% CE-1095 | 4 | 99.1 |
| 100% Solvent M | 4 | 89 |

Solvent M containing microalgal derived methyl ester was found to be efficacious in removing bitumen, used drilling mud, and crude oil.

Example 5

Cleaning Formulations

Cleaning compositions containing microalgal derived alkyl esters can be prepared as shown in Table 8.

TABLE 8

FORMULATIONS CONTAINING ALGAL ALKYL ESTER.

| Use | Ingredients | Wt % |
|---|---|---|
| All-Purpose cleaner concentrate | Algal alkyl ester | 7.95 |
| | d-limonene tech grade | 1.98 |
| | NINOL 11-CM | 68.41 |
| | Westvaco L-5 fatty acid | 6.08 |
| | Triethanol amine, 99% | 3.42 |
| | D.I. water | 6.08 |
| | Polyproylene glycol | 6.08 |
| Multipurpose cleaner | NINOL 11-CM | 82.14 |
| | Algal alkyl ester | 17.86 |
| | Above Blend | 24.19 |
| | Butyl Carbitol Solvent Butoxydiglycol (Dow) | 4.81 |
| | Versene 100 Tetrasodium EDTA (Dow) | 3.21 |
| | D.I. water | q.s. to 100 |
| Laundry pre-spotter | Algal alkyl ester | 56 |
| | BIO-SOFT N25-7 | 19 |
| | BIO-SOFT N25-3 | 19 |
| | Ethanol | 4 |
| | D.I. water | 2 |
| Concrete cleaner | Algal alkyl ester | 70 |
| | Ethyl lactate | 20 |
| | BIO-SOFT EC-690 | 10 |
| | Fragrance (optional) | q.s. |
| Concrete oil stain remover | Algal alkyl ester | 50 |
| | d-limonene tech grade | 25 |
| | C 12-15, 9 mole ethoxylated alcohol surfactant | 25 |
| Parts washer solvent | Algal alkyl ester | 75 |
| | Ethyl lactate | 10 |
| | BIO-SOFT N1-7 | 10 |
| | d-limonene tech grade | 5 |
| Degreaser/cleaner | Algal alkyl ester | 5-35 |
| | Dodecylbenzensulfonic acid | 5-10 |
| | Linear alcohol ethoxylate (6-10 mole) | 5-10 |
| | Sodium xylene sulfonate | qs to pH 4 or greater |
| | Water | qs to 100 |
| Parts Cleaner/Degreaser | Algal alkyl ester | 90-100 |
| | C 12-15, 9 mole ethoxylated alcohol surfactant | 0-10 |
| Floating Lift Station Degreaser | Algal alkyl ester | 70 |
| | d-limonene tech grade | 30 |
| Heavy Duty Degreaser | Algal alkyl ester | 20 |
| | NINOL 11-CM | 20 |
| | MAKON 8 | 10 |
| | BIO-TERGE PAS-8S | 10 |
| | D.I. water | qs to 100 |
| Animal Fat Degreaser/Grease trap opener | Algal alkyl ester | 25 |
| | d-limonene tech grade | 75 |
| Engine degreaser/high pressure chamber wash degreaser | Algal alkyl ester | 50 |
| | Ethyl lactate | 10 |
| | Dibutyl ether | 5 |
| | Ethoxylated nonyl phenol | 5 |
| | Defoamer | 3 |
| | Mineral Oil | 27 |
| Graffiti Remover | Algal alkyl ester | 62-65 |
| | Ethyl lactate | 25 |
| | ViscoAbit (React) | 5 |
| | NP9 or equivalent | 4.95 |
| | Fragrance (optional) | 0-3 |
| | BHT | 0.05 |
| Graffiti Remover | Algal alkyl ester | 52-55 |
| | NMP | 20 |
| | Ethyl lactate | 15 |
| | ViscoAbit (React) | 5 |
| | NP9 or equivalent | 4.95 |
| | Fragrance (optional) | 0-3 |
| | BHT | 0.05 |
| Graffiti Remover | Algal alkyl ester | 85 |
| | BIO-SOFT N1-7 | 10 |
| | Methocel 311 | 5 |
| Thick Paint Stripper | Vertec Gold 50/50 | 74 |
| | Algal alkyl ester | 11 |
| | Nonyl phenol ethoxylate (6 mol) | 6 |
| | Klucerl-H or Methocel 311 (thickener) | 6 |
| | Fragrance | 3 |

TABLE 8-continued

FORMULATIONS CONTAINING ALGAL ALKYL ESTER.

| Use | Ingredients | Wt % |
|---|---|---|
| Paint Stripper | Vertec Gold 50/50 | 74 |
| | Algal alkyl ester | 11 |
| | Tergitol 15-S-59 | 6 |
| | Klucerl-H or Methocel 311 (thickener) | 6 |
| | Fragrance | 3 |
| Varnish remover | Algal alkyl ester | 40 |
| | Ethyl lactate | 10 |
| | d-limonene tech grade | 46 |
| | Ethanol | 4 |
| Screen printing ink cleaner-textile inks | Algal alkyl ester | 85 |
| | BIO-SOFT EC-690 | 15 |
| Printing ink cleaner | Algal alkyl ester | 64 |
| | Dimethyl glutarate, dimethyl adipate, dimethyl succinate | 20 |
| | BIO-SOFT N1-7 | 12 |
| | d-limonene tech grade (fragrance) | 4 |
| Form release agent | Algal alkyl ester | 85 |
| | STEPAN GMO (glyceryl monooleate) | 15 |
| Tar asphalt remover | Algal alkyl ester | 90 |
| | C 12-15, 9 mole ethoxylated alcohol surfactant | 10 |
| Waterless Hand Cleaner | Phase 1: | |
| | Algal alkyl ester | 34 |
| | NINOL 40-CO | 4.5 |
| | MAKON 10 | 10.9 |
| | Oleic acid | 1.7 |
| | Soulan 75 (Amerchol) PEG 75 Lanolin | 0.5 |
| | Phase 2: | |
| | Triethanol amine, 99% | 0.4 |
| | Preservative | qs |
| | D.I. water | qs to 100 |
| Thick gel waterless hand cleaner | Algal alkyl ester | 65 |
| | Ethyl lactate | 10 |
| | BIO-SOFT N1-7 | 15 |
| | ViscoAbit (React) | 10 |
| Hand Cleaner | Algal alkyl ester | 25 |
| | E-Z-Mulse | 45 |
| | Glycerin | 1 |
| | Lanolin | 3 |
| | Water | 26 |
| Hand cleaner | Part A: | |
| | Algal alkyl ester | 30 |
| | Ethylene glycol monostearate | 10 |
| | Calsuds CD-6 (Pilot Chemical) | 11 |
| | Deoderized lanolin | 0.5 |
| | Part B: | |
| | Propylene glycol | 5 |
| | Glycerin | 0.5 |
| | Water | 42.5 |
| | Preservative and Fragrance | 0.5 |

```
SEQUENCE LISTING
SEQ ID MO: 1
pSZ1413; SAD2B::CrTUB2-ScSUC2-CpEF1:PmAMT3-PmFADtp_CwFATB2-CvNR:SAD2B
    1 cactggcagc agccactggt aacaggatta gcagagcgag gtatgtaggc ggtgctacag 61 agttcttgaa gtggtggcct aactacggct acactagaag gacagtattt ggtatctgcg 121 ctctgctgaa gccagttacc ttcggaaaaa gagttggtag ctcttgatcc ggcaaacaaa 181 ccaccgctgg tagcggtggt ttttttgttt gcaagcagca gattacgcgc agaaaaaaag 241 gatctcaaga agatcctttg atcttttcta cggggtctga cgctcagtgg aacgaaaact 301 cacgttaagg gattttggtc atgagattat caaaaaggat cttcacctag atccttttaa 361 attaaaaatg aagttttaaa tcaatctaaa gtatatatga gtaaacttgg tctgacagtt 421 accaatgctt aatcagtgag gcacctatct cagcgatctg tctatttcgt tcatccatag 481 ttgcctgact ccccgtcgtg tagataacta cgatacggga gggcttacca tctggcccca
```

-continued

```
 541 gtgctgcaat gataccgcga gacccacgct caccggctcc agatttatca gcaataaacc 601 agccagccgg aagggccgag cgcagaagtg gtcctgcaac tttatccgcc tccatccagt 661 ctattaattg ttgccgggaa gctagagtaa gtagttcgcc agttaatagt ttgcgcaacg 721 ttgttgccat tgctacaggc atcgtggtgt cacgctcgtc gtttggtatg gcttcattca 781 gctccggttc ccaacgatca aggcgagtta catgatcccc catgttgtgc aaaaaagcgg 841 ttagctcctt cggtcctccg atcgttgtca gaagtaagtt ggccgcagtg ttatcactca 901 tggttatggc agcactgcat aattctctta ctgtcatgcc atccgtaaga tgcttttctg 961 tgactggtga gtactcaacc aagtcattct gagaatagtg tatgcggcga ccgagttgct 1021 cttgcccggc gtcaatacgg gataataccg cgccacatag cagaacttta aaagtgctca 1081 tcattggaaa acgttcttcg gggcgaaaac tctcaaggat cttaccgctg ttgagatcca 1141 gttcgatgta acccactcgt gcacccaact gatcttcagc atcttttact ttcaccagcg 1201 tttctgggtg agcaaaaaca ggaaggcaaa atgccgcaaa aaagggaata agggcgacac 1261 ggaaatgttg aatactcata ctcttccttt ttcaatatta ttgaagcatt tatcagggtt 1321 attgtctcat gagcggatac atatttgaat gtatttagaa aaataaacaa ataggggttc 1381 cgcgcacatt tccccgaaaa gtgccacctg acgtctaaga aaccattatt atcatgacat 1441 taacctataa aaataggcgt atcacgaggc cctttcgtct cgcgcgtttc ggtgatgacg 1501 gtgaaaacct ctgacacatg cagctcccgg agacggtcac agcttgtctg taagcggatg 1561 ccgggagcag acaagcccgt cagggcgcgt cagcgggtgt tggcgggtgt cggggctggc 1621 ttaactatgc ggcatcagag cagattgtac tgagagtgca ccatatgcgg tgtgaaatac 1681 cgcacagatg cgtaaggaga aaataccgca tcaggcgcca ttcgccattc aggctgcgca 1741 actgttggga agggcgatcg gtgcgggcct cttcgctatt acgccagctg gcgaaagggg 1801 gatgtgctgc aaggcgatta agttgggtaa cgccagggtt ttcccagtca cgacgttgta 1861 aaacgacggc cagtgaattg atgcatgctc ttccgcctgg agctggtgca gagcatgggg 1921 cagtttgcgg aggagagggt gctccccgtg ctgcaccccg tggacaagct gtggcagccg 1981 caggacttcc tgcccgaccc cgagtcgccc gacttcgagg accaggtggc ggagctgcgc 2041 gcgcgcgcca aggacctgcc cgacgagtac tttgtggtgc tggtgggcga catgatcacg 2101 gaggaggcgc tgccgaccta catggccatg ctcaacacct tggacggtgt gcgcgacgac 2161 acgggcgcgg ctgaccaccc gtgggcgcgc tggacgcggc agtgggtggc cgaggagaac 2221 cggcacggcg acctgctgaa caagtactgt tggctgacgg ggcgcgtcaa catgcgggcc 2281 gtggaggtga ccatcaacaa cctgatcaag agcggcatga cccgcagac ggacaacaac 2341 ccttacttgg gcttcgtcta cacctccttc caggagcgcg ccaccaagta ggtaccctt 2401 cttgcgctat gacacttcca gcaaaaggta gggcgggctg cgagacggct tcccggcgct 2461 gcatgcaaca ccgatgatgc ttcgaccccc gaagctcct tcggggctgc atgggcgctc 2521 cgatgccgct ccagggcgag cgctgtttaa atagccaggc ccccgattgc aaagacatta 2581 tagcgagcta ccaaagccat attcaaacac ctagatcact accacttcta cacaggccac 2641 tcgagcttgt gatcgcactc cgctaagggg gcgcctcttc ctcttcgttt cagtcacaac 2701 ccgcaaactc tagaatatca atgctgctgc aggccttcct gttcctgctg gccggcttcg 2761 ccgccaagat cagcgcctcc atgacgaacg agacgtccga ccgcccctg gtgcacttca 2821 cccccaacaa gggctggatg aacgacccca acggcctgtg gtacgacgag aaggacgcca 2881 agtggcacct gtacttccag tacaacccga acgacaccgt ctgggggacg cccttgttct 2941 ggggccacgc cacgtccgac gacctgacca actgggagga ccagcccatc gccatcgccc
```

-continued

```
3001 cgaagcgcaa cgactccggc gccttctccg gctccatggt ggtggactac aacaacacct
3061 ccggcttctt caacgacacc atcgacccgc gccagcgctg cgtggccatc tggacctaca
3121 acaccccgga gtccgaggag cagtacatct cctacagcct ggacggcggc tacaccttca
3181 ccgagtacca gaagaacccc gtgctggccg ccaactccac ccagttccgc gacccgaagg
3241 tcttctggta cgagccctcc cagaagtgga tcatgaccgc ggccaagtcc caggactaca
3301 agatcgagat ctactcctcc gacgacctga agtcctggaa gctggagtcc gcgttcgcca
3361 acgagggctt cctcggctac cagtacgagt gccccggcct gatcgaggtc cccaccgagc
3421 aggaccccag caagtcctac tgggtgatgt tcatctccat caaccccggc gccccggccg
3481 gcggctcctt caaccagtac ttcgtcggca gcttcaacgg cacccacttc gaggccttcg
3541 acaaccagtc ccgcgtggtg gacttcggca aggactacta cgccctgcag accttcttca
3601 acaccgaccc gacctacggg agcgccctgg gcatcgcgtg ggcctccaac tgggagtact
3661 ccgccttcgt gcccaccaac ccctggcgct cctccatgtc cctcgtgcgc aagttctccc
3721 tcaacaccga gtaccaggcc aacccggaga cggagctgat caacctgaag gccgagccga
3781 tcctgaacat cagcaacgcc ggcccctgga gccggttcgc caccaacacc acgttgacga
3841 aggccaacag ctacaacgtc gacctgtcca acagcaccgg caccctggag ttcgagctgg
3901 tgtacgccgt caacaccacc cagacgatct ccaagtccgt gttcgcggac ctctccctct
3961 ggttcaaggg cctggaggac cccgaggagt acctccgcat gggcttcgag gtgtccgcgt
4021 cctccttctt cctggaccgc gggaacagca aggtgaagtt cgtgaaggag aacccctact
4081 tcaccaaccg catgagcgtg aacaaccagc ccttcaagag cgagaacgac ctgtcctact
4141 acaaggtgta cggcttgctg gaccagaaca tcctggagct gtacttcaac gacggcgacg
4201 tcgtgtccac caacacctac ttcatgacca ccgggaacgc cctgggctcc gtgaacatga
4261 cgacggggt ggacaacctg ttctacatcg acaagttcca ggtgcgcgag gtcaagtgac
4321 aattgacgga gcgtcgtgcg ggagggagtg tgccgagcgg ggagtcccgg tctgtgcgag
4381 gcccggcagc tgacgctggc gagccgtacg ccccgagggt cccctccc tgcaccctct
4441 tccccttccc tctgacggcc gcgcctgttc ttgcatgttc agcgacggat cccgcgtctc
4501 gaacagagcg cgcagaggaa cgctgaaggt ctcgcctctg tcgcacctca gcgcggcata
4561 caccacaata accacctgac gaatgcgctt ggttcttcgt ccattagcga agcgtccggt
4621 tcacacacgt gccacgttgg cgaggtggca ggtgacaatg atcggtggag ctgatggtcg
4681 aaacgttcac agcctaggga tatcgaattc ggccgacagg acgcgcgtca aaggtgctgg
4741 tcgtgtatgc cctggccggc aggtcgttgc tgctgctggt tagtgattcc gcaaccctga
4801 ttttggcgtc ttattttggc gtggcaaacg ctggcgcccg cgagccgggc cggcggcgat
4861 gcggtgcccc acggctgccg gaatccaagg gaggcaagag cgcccgggtc agttgaaggg
4921 ctttacgcgc aaggtacagc cgctcctgca aggctgcgtg gtggaattgg acgtgcaggt
4981 cctgctgaag ttcctccacc gcctcaccag cggacaaagc accggtgtat caggtccgtg
5041 tcatccactc taaagaactc gactacgacc tactgatggc cctagattct tcatcaaaaa
5101 cgcctgagac acttgcccag gattgaaact ccctgaaggg accaccaggg gccctgagtt
5161 gttccttccc cccgtggcga gctgccagcc aggctgtacc tgtgatcgag gctggcggga
5221 aaataggctt cgtgtgctca ggtcatggga ggtgcaggac agctcatgaa acgccaacaa
5281 tcgcacaatt catgtcaagc taatcagcta tttcctcttc acgagctgta attgtcccaa
5341 aattctggtc taccggggt gatccttcgt gtacgggccc ttccctcaac cctaggtatg
```

-continued

```
5401 cgcgcatgcg gtcgccgcgc aactcgcgcg agggccgagg gtttgggacg ggccgtcccg 5461 aaatgcagtt gcacccggat gcgtggcacc tttttttgcga taatttatgc aatggactgc 5521 tctgcaaaat tctggctctg tcgccaaccc taggatcagc ggcgtaggat ttcgtaatca 5581 ttcgtcctga tggggagcta ccgactaccc taatatcagc ccgactgcct gacgccagcg 5641 tccactttg tgcacacatt ccattcgtgc ccaagacatt tcattgtggt gcgaagcgtc 5701 cccagttacg ctcacctgtt tcccgacctc cttactgttc tgtcgacaga gcgggcccac 5761 aggccggtcg cagccactag tatggctatc aagacgaaca ggcagcctgt ggagaagcct 5821 ccgttcacga tcgggacgct gcgcaaggcc atccccgcgc actgtttcga gcgctcggcg 5881 cttcgtgggc gcgcccccaa ggccaacggc agcgccgtga gcctgaagtc cggcagcctg 5941 aacaccctgg aggacccccc cagcagcccc ccccccgca ccttcctgaa ccagctgccc 6001 gactggagcc gcctgcgcac cgccatcacc accgtgttcg tggccgccga gaagcagttc 6061 acccgcctgg accgcaagag caagcgcccc gacatgctgg tggactggtt cggcagcgag 6121 accatcgtgc aggacggcct ggtgttccgc gagcgcttca gcatccgcag ctacgagatc 6181 ggcgccgacc gcaccgccag catcgagacc ctgatgaacc acctgcagga caccagcctg 6241 aaccactgca gagcgtgggg cctgctgaac gacggcttcg gccgcacccc cgagatgtgc 6301 acccgcgacc tgatctgggt gctgaccaag atgcagatcg tggtgaaccg ctaccccacc 6361 tggggcgaca ccgtggagat caacagctgg ttcagccaga gcggcaagat cggcatgggc 6421 cgcgagtggc tgatcagcga ctgcaacacc ggcgagatcc tggtgcgcgc caccagcgcc 6481 tgggccatga tgaaccagaa gacccgccgc ttcagcaagc tgccctgcga ggtgcgccag 6541 gagatcgccc cccacttcgt ggacgccccc cccgtgatcg aggacaacga ccgcaagctg 6601 cacaagttcg acgtgaagac cggcgacagc atctgcaagg gcctgacccc cggctggaac 6661 gacttcgacg tgaaccagca cgtgagcaac gtgaagtaca tcggctggat tctggagagc 6721 atgcccaccg aggtgctgga gacccaggag ctgtgcagcc tgaccctgga gtaccgccgc 6781 gagtgcggcc gcgagagcgt ggtggagagc gtgaccagca tgaaccccag caaggtgggc 6841 gaccgcagcc agtaccagca cctgctgcgc ctggaggacg cgccgacat catgaagggc 6901 cgcaccgagt ggcgcccaa gaacgccggc accaaccgcg ccatcagcac ctgattaatt 6961 aactcgaggc agcagcagct cggatagtat cgacacactc tggacgctgg tcgtgtgatg 7021 gactgttgcc gccacacttg ctgccttgac ctgtgaatat ccctgccgct tttatcaaac 7081 agcctcagtg tgtttgatct tgtgtgtacg cgcttttgcg agttgctagc tgcttgtgct 7141 atttgcgaat accaccccca gcatcccctt ccctcgtttc atatcgcttg catcccaacc 7201 gcaacttatc tacgctgtcc tgctatccct cagcgctgct cctgctcctg ctcactgccc 7261 ctcgcacagc cttggtttgg gctccgcctg tattctcctg gtactgcaac ctgtaaacca 7321 gcactgcaat gctgatgcac gggaagtagt gggatgggaa cacaaatgga aagcttgagc 7381 tccagccacg gcaacaccgc gcgccttgcg gccgagcacg gcgacaagaa cctgagcaag 7441 atctgcgggc tgatcgccag cgacgagggc cggcacgaga tcgcctacac gcgcatcgtg 7501 gacgagttct tccgcctcga ccccgagggc gccgtcgccg cctacgccaa catgatgcgc 7561 aagcagatca ccatgcccgc gcacctcatg gacgacatgg ccacggcga ggccaacccg 7621 ggccgcaacc tcttcgccga cttctccgcg gtcgccgaga gatcgacgt ctacgacgcc 7681 gaggactact gccgcatcct ggagcacctc aacgcgcgct ggaaggtgga cgagcgccag 7741 gtcagcggcc aggccgccgc ggaccaggag tacgtcctgg gcctgccca gcgcttccgg 7801 aaactcgccg agaagaccgc cgccaagcgc aagcgcgtcg cgcgcaggcc cgtcgccttc
```

-continued

```
7861 tcctggagaa gagcctctag agtcgacctg caggcatgca agcttggcgt aatcatggtc 7921 atagctgttt cctgtgtgaa attgttatcc gctcacaatt ccacacaaca tacgagccgg 7981 aagcataaag tgtaaagcct ggggtgccta atgagtgagc taactcacat taattgcgtt 8041 gcgctcactg cccgctttcc agtcgggaaa cctgtcgtgc cagctgcatt aatgaatcgg 8101 ccaacgcgcg gggagaggcg gtttgcgtat tgggcgctct tccgcttcct cgctcactga 8161 ctcgctgcgc tcggtcgttc ggctgcggcg agcggtatca gctcactcaa aggcggtaat 8221 acggttatcc acagaatcag gggataacgc aggaaagaac atgtgagcaa aaggccagca 8281 aaaggccagg aaccgtaaaa aggccgcgtt gctggcgttt ttccataggc tccgcccccc 8341 tgacgagcat cacaaaaatc gacgctcaag tcagaggtgg cgaaacccga caggactata 8401 aagataccag gcgtttcccc ctggaagctc cctcgtgcgc tctcctgttc cgaccctgcc 8461 gcttaccgga tacctgtccg cctttctccc ttcgggaagc gtggcgcttt ctcatagctc 8521 acgctgtagg tatctcagtt cggtgtaggt cgttcgctcc aagctgggct gtgtgcacga 8581 accccccgtt cagcccgacc gctgcgcctt atccggtaac tatcgtcttg agtccaaccc 8641 ggtaagacac gacttatcgc
```

What is claimed is:

1. A composition comprising C1-C4 esters of fatty acids derived from triglyceride oil produced by a microalga that is a recombinant oleaginous cell of the genus *Prototheca*, the oil having an altered fatty acid profile relative to an oil produced by a non-recombinant microalga of the genus *Prototheca*, the altered fatty acid profile having at least 10% C10:0 and 40% C12:0 fatty acids, the composition having a reduced odor compared to a composition where all the fatty acids are derived from vegetable or animal triglyceride oil having a fatty acid profile of at least 40% C12:0 fatty acids.

2. The composition of claim 1, wherein the odor is an unpleasant odor characteristic of a C6 or C8 fatty acid or ester thereof.

3. The composition of claim 1, wherein the ester is a methyl, ethyl, propyl, iso-propyl, butyl, or a tert-butyl ester.

4. The composition of claim 1, having an altered fatty acid profile wherein C12:0>C10:0>C14:0.

5. The composition of claim 1, wherein at least 50% of the fatty acids are C12:0 fatty acids or the combined total amount of C:10 and C:12 fatty acids is at least 60%.

6. The composition of claim 1, wherein at least 15% of the fatty acids are C10:0 fatty acids.

7. The composition of claim 1, wherein 15-25% of the fatty acids are C10:0 fatty acids.

8. The composition of claim 1, wherein 10-15% of the fatty acids are C14:0 fatty acids.

9. The composition of claim 1, wherein less than 8%, 7%, or 6% of the fatty acids are C16:0 fatty acids.

10. The composition of claim 1, wherein less than 0.5% of the fatty acids are C8:0 fatty acids.

11. The composition of claim 1, wherein less than 0.1%, 0.01%, or 0.001% of the fatty acids are C6:0 fatty acids.

12. The composition of claim 1, comprising a terpene.

13. The composition of claim 12, wherein the terpene is limonene.

14. A method for preparing a composition comprising C1-C4 esters of fatty acids derived from triglyceride oil produced by a microalga of the genus *Prototheca*, the composition having a reduced odor compared to a composition where all the fatty acids are derived from vegetable oil, the method comprising:
   a) providing oil produced by a microalga that is a recombinant oleaginous cell of the genus *Prototheca*, the oil comprising triacylglycerides having an altered fatty acid profile relative to an oil produced by a non-recombinant microalga of the genus *Prototheca*, wherein the most abundant fatty acids are C12:0 fatty acids; and
   b) treating the triacylglycerides with a C1-C4 alcohol under transesterification conditions to form C1-C4 esters of the microalgal derived fatty acids.

15. The method of claim 14, wherein the C1-C4 alcohol is methanol, ethanol, propanol, iso-propanol, butanol, or a tert-butanol.

16. The method of claim 14 further comprising blending the C1-C4 esters of fatty acids with one or more of a terpene, a C1-C4 ester of lactic acid, a surfactant, an emulsifier, or water.

* * * * *